United States Patent
Wakai et al.

(10) Patent No.: US 10,140,752 B2
(45) Date of Patent: Nov. 27, 2018

(54) MEDICAL IMAGE PROCESSING SYSTEM, MEDICAL IMAGE PROCESSING APPARATUS, MEDICAL IMAGE DIAGNOSIS APPARATUS, AND MEDICAL IMAGE PROCESSING METHOD, RELATED TO A STEREOSCOPIC MEDICAL IMAGE PROCESS

(71) Applicant: Toshiba Medical Systems Corporation, Otawara-shi (JP)

(72) Inventors: Satoshi Wakai, Nasushiobara (JP); Yoshiyuki Kokojima, Yokohama (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/048,904

(22) Filed: Oct. 8, 2013

(65) Prior Publication Data

US 2014/0035910 A1 Feb. 6, 2014

Related U.S. Application Data

(63) Continuation of application No. PCT/JP2012/059584, filed on Apr. 6, 2012.

(30) Foreign Application Priority Data

Apr. 8, 2011 (JP) ................................. 2011-086636

(51) Int. Cl.
*H04N 13/00* (2018.01)
*G06T 15/08* (2011.01)
(Continued)

(52) U.S. Cl.
CPC .............. *G06T 15/08* (2013.01); *A61B 5/055* (2013.01); *A61B 6/022* (2013.01); *A61B 6/466* (2013.01);
(Continued)

(58) Field of Classification Search
CPC ........... H04N 13/0029; H04N 13/0011; H04N 13/0044; H04N 13/0282
(Continued)

(56) References Cited

U.S. PATENT DOCUMENTS 7,567,648 B2 * 7/2009 Tsubaki et al. ................. 378/41
2006/0039529 A1 2/2006 Tsubaki et al.
(Continued)

FOREIGN PATENT DOCUMENTS

CN 101 984 670 A 3/2011
JP 11-306326 A 11/1999
(Continued)

OTHER PUBLICATIONS

Jeffrey S. McVeigh ; Victor S. Grinberg ; Mel Siegel; Double-buffering technique for binocular imaging in a window. Proc. SPIE 2409, Stereoscopic Displays and Virtual Reality Systems II, 168 (Mar. 30, 1995).*

(Continued)

*Primary Examiner* — Shivang Patel
(74) *Attorney, Agent, or Firm* — Oblon, McClelland, Maier & Neustadt, L.L.P.

(57) ABSTRACT

A medical image diagnosis system according to an embodiment includes a determining unit, a rendering processing unit, and an output unit. The determining unit is configured to, based on information related to a stereoscopic function of a display unit connected to an output target apparatus serving as an output target, determine a parallax image number of images that are for realizing a stereoscopic view and are to be displayed by the display unit. The rendering processing unit is configured to generate rendering images corresponding to the parallax image number, by performing a rendering process on volume data that represents three-dimensional medical images. The output unit is configured (Continued)

to output the rendering images corresponding to the parallax image number to the output target apparatus, as the images that are for realizing the stereoscopic view and are to be simultaneously displayed by the display unit.

12 Claims, 18 Drawing Sheets

(51) Int. Cl.
| | |
|---|---|
| *A61B 5/055* | (2006.01) |
| *A61B 6/00* | (2006.01) |
| *A61B 8/00* | (2006.01) |
| *A61B 6/02* | (2006.01) |
| *A61B 8/08* | (2006.01) |
| *H04N 13/02* | (2006.01) |
| *H04N 13/04* | (2006.01) |
| *A61B 5/00* | (2006.01) |

(52) U.S. Cl.
CPC ............ *A61B 6/5211* (2013.01); *A61B 8/466* (2013.01); *A61B 8/483* (2013.01); *A61B 8/5215* (2013.01); *H04N 13/0007* (2013.01); *H04N 13/0282* (2013.01); *H04N 13/0438* (2013.01); *A61B 5/7207* (2013.01); *A61B 2576/023* (2013.01); *H04N 2213/007* (2013.01)

(58) Field of Classification Search
USPC ......................................................... 345/419
See application file for complete search history.

(56) References Cited

U.S. PATENT DOCUMENTS

| | | | |
|---|---|---|---|
| 2006/0170674 A1 | 8/2006 | Tsubaki et al. | |
| 2008/0095308 A1 | 4/2008 | Kano | |
| 2011/0235066 A1* | 9/2011 | Sakuragi | ............... G06T 7/0022 |
| | | | 358/1.6 |
| 2013/0335408 A1* | 12/2013 | Yi et al. | ........................ 345/419 |

FOREIGN PATENT DOCUMENTS

| | | |
|---|---|---|
| JP | 2005-086414 A | 3/2005 |
| JP | 2005-136594 A | 5/2005 |
| JP | 2005-349127 A | 12/2005 |
| JP | 2006-101329 | 4/2006 |
| JP | 2006-212056 A | 8/2006 |
| JP | 3944188 | 4/2007 |
| JP | 4125252 | 5/2008 |
| JP | 2009-273672 A | 11/2009 |
| JP | 2011-234788 A | 11/2011 |
| WO | WO 2009/120196 A1 | 10/2009 |

OTHER PUBLICATIONS

International Search Report dated Jul. 17, 2012 for PCT/JP2012/059584 filed on Apr. 6, 2012 with English Translation.
International Written Opinion dated Jul. 17, 2012 for PCT/JP2012/059584 filed on Apr. 6, 2012.
Masahiro Sekine, "Rittaibutsu o Tegaru ni Satsuei Dekiru Scan-gata 3D Satsuei System", Toshiba Review, 2009, vol. 64, No. 5, pp. 62-63.
Chinese Office Action dated May 6, 2014, in China Patent Application No. 201280000442.5.
Extended Search Report dated Nov. 20, 2014 in European Application No. 12768352.2.

* cited by examiner

| PARALLAX NUMBER | NINE-EYE PARALLAX |
|---|---|
| PARALLAX ANGLE | 1 DEGREE |

| PARALLAX NUMBER | TWO-EYE PARALLAX |
|---|---|
| PARALLAX ANGLE | 4 DEGREES |

| PARALLAX NUMBER | NO PARALLAX |
|---|---|
| PARALLAX ANGLE | |

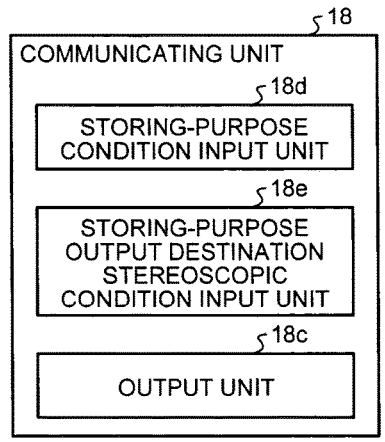
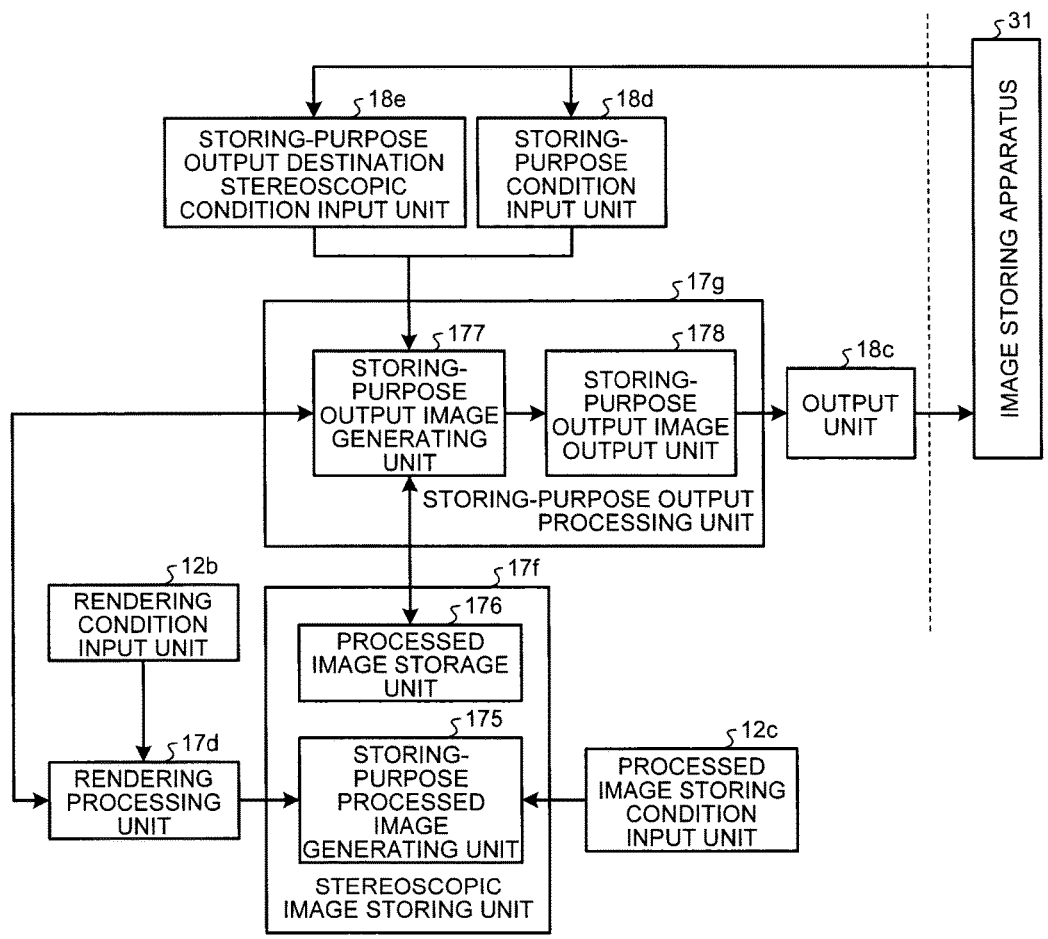

MEDICAL IMAGE PROCESSING SYSTEM, MEDICAL IMAGE PROCESSING APPARATUS, MEDICAL IMAGE DIAGNOSIS APPARATUS, AND MEDICAL IMAGE PROCESSING METHOD, RELATED TO A STEREOSCOPIC MEDICAL IMAGE PROCESS

CROSS-REFERENCE TO RELATED APPLICATIONS

This application is a continuation of PCT international application Ser. No. PCT/JP2012/059584 filed on Apr. 6, 2012 which designates the United States, and which claims the benefit of priority from Japanese Patent Application No. 2011-086636, filed on Apr. 8, 2011; the entire contents of which are incorporated herein by reference.

FIELD

Embodiments described herein relate to a medical image processing system, a medical image processing apparatus, a medical image diagnosis apparatus, and a medical image processing method.

BACKGROUND

Conventionally, such monitors have been in practical use that are capable of providing a stereoscopic view of two-eye parallax images (binocular parallax images) taken from two viewpoints, by using an exclusive-use device such as stereoscopic glasses or the like. Further, in recent years, such monitors have also been in practical use that are capable of providing, for a viewer with naked eyes, a stereoscopic view of multiple-eye parallax images (e.g., nine-eye parallax images) taken from a plurality of viewpoints, by using a light beam controller such as a lenticular lens. Two-eye parallax images and nine-eye parallax images that are displayed on a monitor capable of providing a stereoscopic view may be generated, in some situations, by estimating depth information of an image taken from one viewpoint and performing image processing while using the estimated information.

As for medical image diagnosis apparatuses such as X-ray Computed Tomography (CT) apparatuses, Magnetic Resonance Imaging (MRI) apparatuses, and ultrasound diagnosis apparatuses, apparatuses that are capable of generating three-dimensional medical images (volume data) have been in practical use. Conventionally, the volume data generated by such a medical image diagnosis apparatus is arranged to be a two-dimensional image (a rendering image) by performing various types of image processing processes (rendering processes) and is displayed in a two-dimensional manner on a general-purpose monitor. For example, the volume data generated by such a medical image diagnosis apparatus is arranged to be a two-dimensional image (a volume rendering image) that reflects three-dimensional information by performing a volume rendering process and is displayed in a two-dimensional manner on a general-purpose monitor.

However, even if the two-dimensional volume rendering image generated from the volume data is displayed on the general-purpose monitor, it is not possible to stereoscopically reproduce complicated structures of a human body rendered in the volume rendering image. Further, specifications related to the stereoscopic method used by a monitor may vary depending on the medical image diagnosis apparatus and apparatuses connected to the medical image diagnosis apparatus.

BRIEF DESCRIPTION OF DRAWINGS

FIG. 20 is a drawing for explaining an exemplary configuration of a communicating unit according to a fourth embodiment.

FIG. 21 is a block diagram for explaining processes performed by a rendering processing unit, a stereoscopic image storing unit, a storing-purpose output processing unit, and an output unit according to the fourth embodiment.

DETAILED DESCRIPTION

A medical image diagnosis system according to an embodiment includes a determining unit, a rendering processing unit, and an output unit. The determining unit is configured to, based on information related to a stereoscopic function of a display unit connected to an output target apparatus serving as an output target, determine a parallax image number of images that are for realizing a stereoscopic view and are to be displayed by the display unit. The rendering processing unit is configured to generate rendering images corresponding to the parallax image number, by performing a rendering process on volume data that represents three-dimensional medical images. The output unit is configured to output the rendering images corresponding to the parallax image number to the output target apparatus, as the images that are for realizing the stereoscopic view and are to be simultaneously displayed by the display unit.

Exemplary embodiments of a medical image processing system will be explained in detail, with reference to the accompanying drawings. In the following sections, a medical image processing system that includes a medical image diagnosis apparatus having functions of a medical image processing system will be explained as the exemplary embodiments.

First Embodiment

Figure 1:
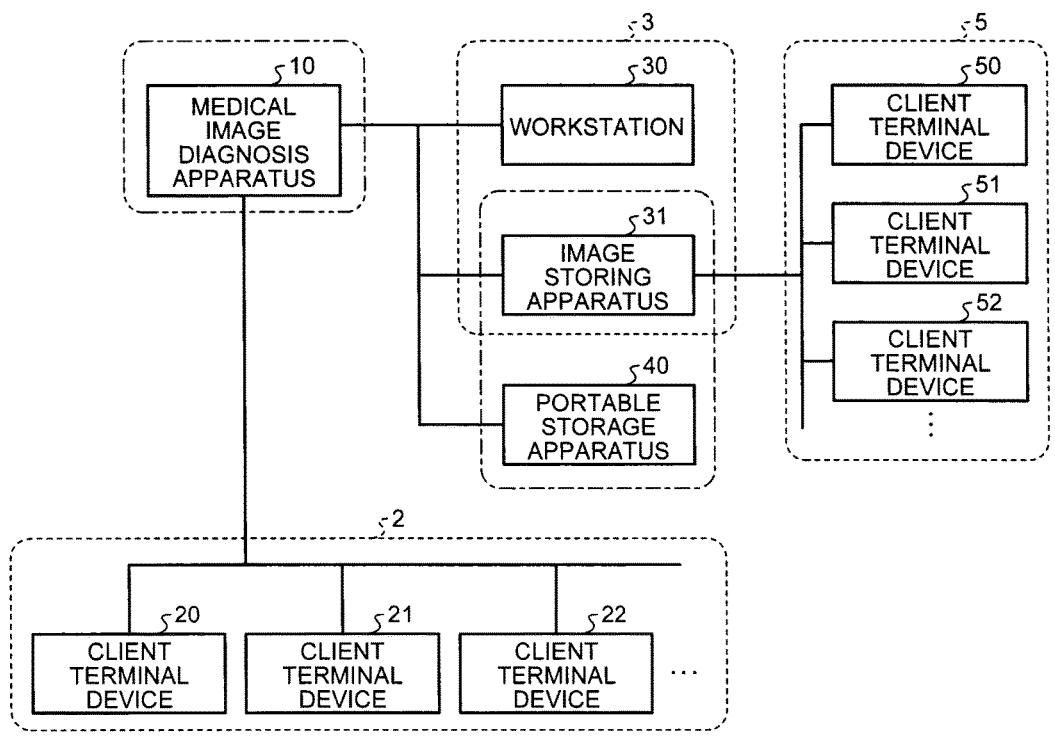
FIG. 1 is a drawing for explaining an exemplary configuration of a medical image processing system according to a first embodiment.

First, an exemplary configuration of a medical image processing system according to a first embodiment will be explained. FIG. 1 is a drawing for explaining the exemplary configuration of the medical image processing system according to the first embodiment.

As shown in FIG. 1, the medical image processing system according to the first embodiment includes a medical image diagnosis apparatus 10, a group of client terminal devices 2 of which each member is connectable to the medical image diagnosis apparatus 10, a group of external apparatuses 3, a portable storage apparatus 40, and a group of client terminal devices 5 of which each member is connectable to the group of external apparatuses 3. The apparatuses illustrated in FIG. 1 are able to communicate with one another directly or indirectly via, for example, an intra-hospital Local Area Network (LAN) provided in a hospital.

The medical image diagnosis apparatus 10 is an apparatus configured to take medical images such as an X-ray diagnosis apparatus, an X-ray Computed Tomography (CT) apparatus, an Magnetic Resonance Imaging (MRI) apparatus, an ultrasound diagnosis apparatus, a Single Photon Emission Computed Tomography (SPECT) apparatus, a Positron Emission computed Tomography (PET) apparatus, a SPECT-CT apparatus having a SPECT apparatus and an X-ray CT apparatus incorporated therein, or a PET-CT apparatus having a PET apparatus and an X-ray CT apparatus incorporated therein. More specifically, the medical image diagnosis apparatus 10 according to the first embodiment is an apparatus capable of generating three-dimensional medical images. In the following sections, three-dimensional medical images will be referred to as "volume data".

The group of client terminal devices 2 is a group of apparatuses each capable of directly accessing the medical image diagnosis apparatus 10 in a wired or wireless manner. As shown in FIG. 1, the group of client terminal devices 2 includes a client terminal device 20, a client terminal device 21, and a client terminal device 22. For example, the group of client terminal devices 2 is a group of apparatuses operated by medical doctors and laboratory technicians working in the hospital and may include Personal Computers (PCs), tablet-type PCs, Personal Digital Assistants (PDAs), portable telephones, and the like.

Further, the group of client terminal devices 5 is a group of apparatuses each capable of directly accessing an image storing apparatus 31 included in the group of external apparatuses 3 (explained later) in a wired or wireless manner. As shown in FIG. 1, the group of client terminal devices 5 includes a client terminal device 50, a client terminal device 51, and a client terminal device 52. For example, like the group of client terminal devices 2, the group of client terminal devices 5 is a group of apparatuses operated by medical doctors and laboratory technicians working in the hospital and may include Personal Computers (PCs), tablet-type PCs, Personal Digital Assistants (PDAs), portable telephones, and the like.

The group of external apparatuses 3 is a group of apparatuses connected to the medical image diagnosis apparatus 10, separately from the group of client terminal devices 2. As shown in FIG. 1, the group of external apparatuses 3 includes a workstation 30 and the image storing apparatus 31. The workstation 30 is a business-use high-performance computer that is specialized in image processing and clerical processing, in contrast to the group of client terminal devices 2 and the group of client terminal devices 5. Further, the image storing apparatus 31 is configured with a database in a Picture Archiving and Communication System (PACS) that manages various types of medical image data, a database of an electronic medical record system that manages electronic medical records to which medical images are attached, or the like.

The portable storage apparatus 40 is configured with a computer-readable storage apparatus such as a hard disk, a flexible disk, a Compact Disk Read-Only Memory (CD-ROM), a Magneto-Optical Disk (MO), a Digital Versatile Disk (DVD), or a Blu-ray Disc (registered trademark), and can be carried away. The portable storage apparatus 40 is a storage apparatus connected to the medical image diagnosis apparatus 10 for the purpose of storing therein various types of images generated by the medical image diagnosis apparatus 10.

As explained above, the medical image diagnosis apparatus 10 according to the first embodiment is an apparatus capable of generating the volume data. Also, the medical image diagnosis apparatus 10 according to the first embodiment further has a function of generating rendering images by performing various types of rendering processes on the volume data. In addition, the medical image diagnosis apparatus 10 according to the first embodiment performs a process to output the rendering images generated from the volume data to the apparatuses explained above.

More specifically, as shown in FIG. 1, the medical image diagnosis apparatus 10 according to the first embodiment serves as an output source of the rendering images. Further, as shown in FIG. 1, the medical image diagnosis apparatus 10 according to the first embodiment uses the group of client terminal devices 2, the group of external apparatuses 3, and the group of client terminal devices 5 as display-purpose output targets of the rendering images. In other words, the medical image diagnosis apparatus 10 according to the first embodiment uses each of monitors (display units) respectively connected to the members of the group of client terminal devices 2, the group of external apparatuses 3, and the group of client terminal devices 5, as an output target that is caused to display the rendering images generated by the medical image diagnosis apparatus 10. Further, although not shown in FIG. 1, the medical image diagnosis apparatus 10 according to the first embodiment also uses a monitor connected thereto, as a display-purpose output target that is caused to display the rendering images generated by the medical image diagnosis apparatus 10.

Further, as shown in FIG. 1, the medical image diagnosis apparatus 10 according to the first embodiment uses the image storing apparatus 31 and the portable storage apparatus 40 included in the group of external apparatuses 3, as storing-purpose output targets of the rendering images. In other words, the medical image diagnosis apparatus 10 according to the first embodiment uses the image storing apparatus 31 and the portable storage apparatus 40, as the output targets that are caused to store therein the rendering images. Further, although not shown in FIG. 1, the medical image diagnosis apparatus 10 according to the first embodiment may also use the workstation 30 as a storing-purpose output target.

Figure 2:
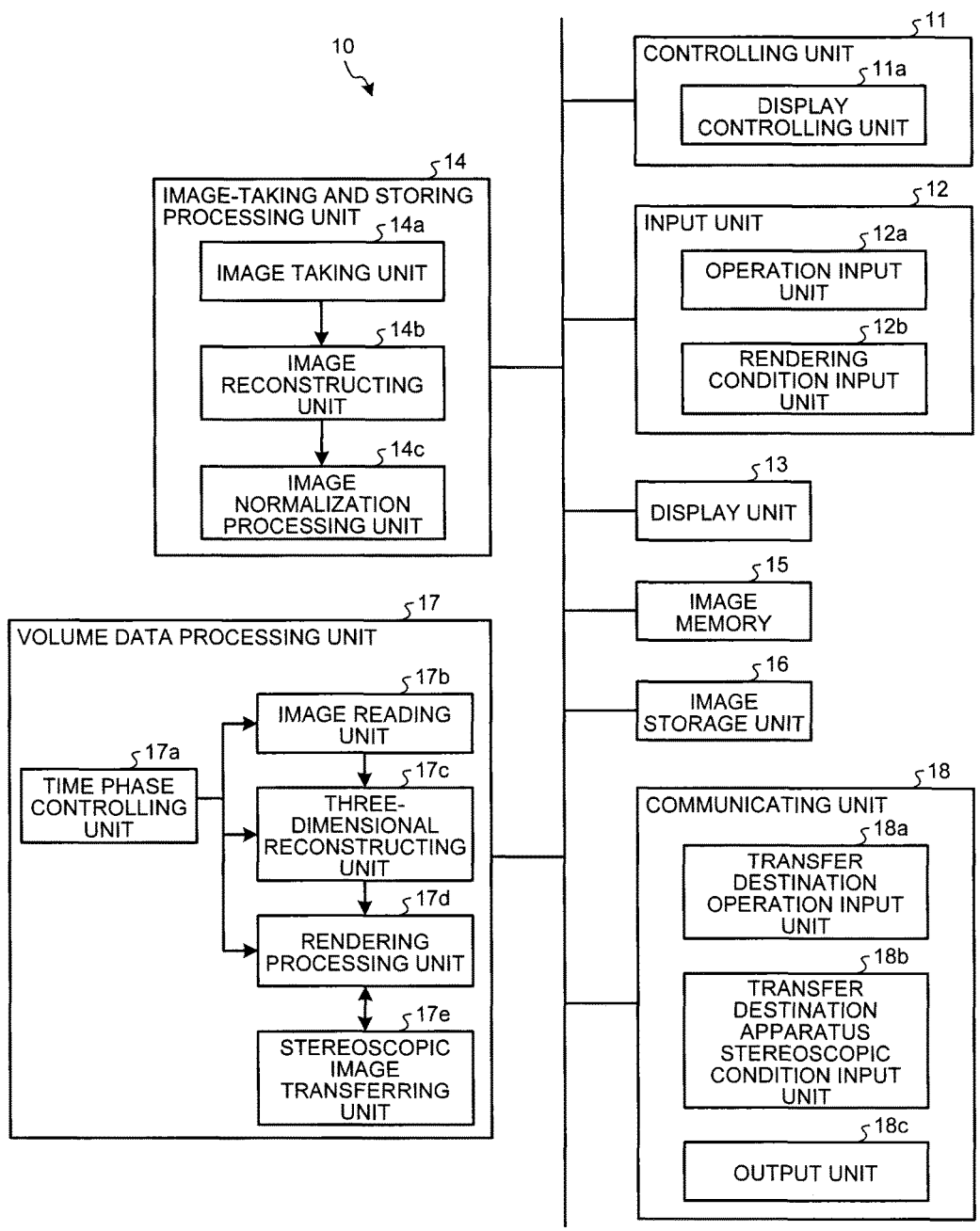
FIG. 2 is a drawing for explaining an exemplary configuration of a medical image diagnosis apparatus according to the first embodiment.

In the following sections, an exemplary configuration of the medical image diagnosis apparatus 10 according to the first embodiment will be explained, with reference to FIG. 2. FIG. 2 is a drawing for explaining the exemplary configuration of the medical image diagnosis apparatus according to the first embodiment.

As shown in FIG. 2, the medical image diagnosis apparatus 10 according to the first embodiment includes a controlling unit 11, an input unit 12, a display unit 13, an image-taking and storing processing unit 14, an image memory 15, an image storage unit 16, a volume data processing unit 17, and a communicating unit 18.

The controlling unit 11 exercises overall control of the medical image diagnosis apparatus 10.

The input unit 12 includes a mouse, a keyboard, a button, a panel switch, a touch command screen, a foot switch, a trackball, a sense-of-force feedback apparatus, and/or the like and is configured to receive various types of setting requests from an operator of the medical image diagnosis apparatus 10 and to transfer the received various types of setting requests to the controlling unit 11. More specifically, as shown in FIG. 2, the input unit 12 includes an operation input unit 12a and a rendering condition input unit 12b. The operation input unit 12a receives, from the operator, information related to a medical-image taking process and a medical-image storing process performed by the image-taking and storing processing unit 14, which is explained later. Further, the rendering condition input unit 12b receives, from the operator, a condition setting related to a rendering process performed by the volume data processing unit 17 on the volume data (explained later).

The display unit 13 displays a Graphical User Interface (GUI) used by the operator of the medical image diagnosis apparatus 10 to input the various types of setting requests through the input unit 12 and also displays medical images taken by the medical image diagnosis apparatus 10 and the like. To control the display processes performed by the display unit 13, the controlling unit 11 includes a display controlling unit 11a, as shown in FIG. 2.

The image-taking and storing processing unit 14 is a processing unit that performs the medical-image taking process and the medical-image storing process and includes an image taking unit 14a, an image reconstructing unit 14b, and an image normalization processing unit 14c. The image taking unit 14a is an apparatus configured to take medical images and corresponds to, for example, a gantry of an MRI apparatus or an X-ray CT apparatus and is configured to acquire MR signals and data such as X-ray projection data.

The image reconstructing unit 14b reconstructs medical images from the data acquired by the image taking unit 14a. For example, from the data acquired by the image taking unit 14a, the image reconstructing unit 14b reconstructs a medical image on an axial plane of a subject who is a target of the image taking process. In another example, from the data acquired by the image taking unit 14a, the image reconstructing unit 14b reconstructs medical images on a plurality of axial planes along a body-axis direction of the subject. As a result of such reconstructing processes, the image reconstructing unit 14b generates three-dimensional medical images (the volume data).

The image normalization processing unit 14c performs a normalization process on the medical images reconstructed by the image reconstructing unit 14b. For example, when the medical image diagnosis apparatus 10 is an MRI apparatus, because the range of the MR signals acquired by the image taking unit 14a varies depending on image taking conditions, the range of pixel values is different for each of a plurality of reconstructed MRI images. However, when a medical-image storing process is performed, the medical image data needs to be collectively put into, for example, 16 bits. For this reason, the image normalization processing unit 14c performs a normalization process expressed as, for example, "$Y=a \times X+b$" by using coefficients "a" and "b", on a medical image (an original image: X) that does not satisfy a storing condition. As a result, the image normalization processing unit 14c generates a stored image (Y) obtained by normalizing the original image (X) into 16-bit information. If the medical image to be stored satisfies the storing condition, the image normalization processing unit 14c does not perform the normalization process.

The image memory 15 is a memory that temporarily stores therein the medical images reconstructed by the image reconstructing unit 14b and the stored images generated by the image normalization processing unit 14c. Further, the image storage unit 16 is configured with a hard disk drive (HDD) that stores therein the data stored in the image memory 15 and the stored images generated by the image normalization processing unit 14c. The image normalization processing unit 14c stores the coefficients used in the normalization process into the image memory 15 and/or the image storage unit 16, in correspondence with the stored images.

The data stored into the image memory 15 and the image storage unit 16 goes through an image processing process performed by the volume data processing unit 17 (explained later) and is subsequently displayed by the display unit 13 under the control of the controlling unit 11. In another example, the data stored into the image memory 15 and the image storage unit 16 goes through an image processing process performed by the volume data processing unit 17

(explained later) and is subsequently output by the communicating unit 18 (explained later) under the control of the controlling unit 11.

It is also acceptable to configure the first embodiment in such a manner that only the image memory 15 is provided, without the image storage unit 16. In such a situation, the data stored in the image memory 15 is deleted, after going through the image processing process performed by the volume data processing unit 17 (explained later) and being output. In the first embodiment, while the image taking process is performed by the image-taking and storing processing unit 14, a volume rendering process is performed in a real-time manner by the volume data processing unit 17 as explained below.

The volume data processing unit 17 is a processing unit that performs the image processing process on the volume data generated by the image reconstructing unit 14b and includes a time phase controlling unit 17a, an image reading unit 17b, a three-dimensional reconstructing unit 17c, a rendering processing unit 17d, and a stereoscopic image transferring unit 17e.

The image reading unit 17b reads the stored images from the image memory 15 or the image storage unit 16. The three-dimensional reconstructing unit 17c reconstructs the volume data from the plurality of stored images read by the image reading unit 17b. For example, the three-dimensional reconstructing unit 17c reconstructs the volume data by three-dimensionally reconstructing 500 stored images on axial planes that were read by the image reading unit 17b, based on pitch widths of the axial planes.

The rendering processing unit 17d performs the rendering process on the volume data reconstructed by the three-dimensional reconstructing unit 17c. More specifically, the rendering processing unit 17d reads the volume data and first performs a pre-processing process on the read volume data. Subsequently, the rendering processing unit 17d generates volume rendering images by performing a volume rendering process on the pre-processed volume data. After that, the rendering processing unit 17d generates a two-dimensional image in which various types of information (a scale mark, the patient's name, tested items, and the like) are rendered and superimposes the generated two-dimensional image onto the volume rendering images so as to generate output-purpose two-dimensional images. The rendering processing unit 17d will be explained in detail later, with reference to FIG. 3.

The time phase controlling unit 17a is a controlling unit that, if a plurality of pieces of volume data to be processed have been generated along a time sequence, controls the image reading unit 17b, the three-dimensional reconstructing unit 17c, and the rendering processing unit 17d so that each of the stored images is processed along an image-taking time thereof.

The stereoscopic image transferring unit 17e is a processing unit that, when transferring a processing result of the rendering processing unit 17d to an apparatus at the output destination via the communicating unit 18 (explained later), converts the processing result to output-purpose (transfer-purpose) data. The stereoscopic image transferring unit 17e will be explained in detail later.

The communicating unit 18 is configured with a Network Interface Card (NIC) or the like and communicates with the apparatuses connected to the medical image diagnosis apparatus 10. More specifically, the communicating unit 18 according to the first embodiment includes a transfer destination operation input unit 18a, a transfer destination apparatus stereoscopic condition input unit 18b, and an output unit 18c. Processes performed by the transfer destination operation input unit 18a, the transfer destination apparatus stereoscopic condition input unit 18b, and the output unit 18c will be explained in detail later.

Figure 3:
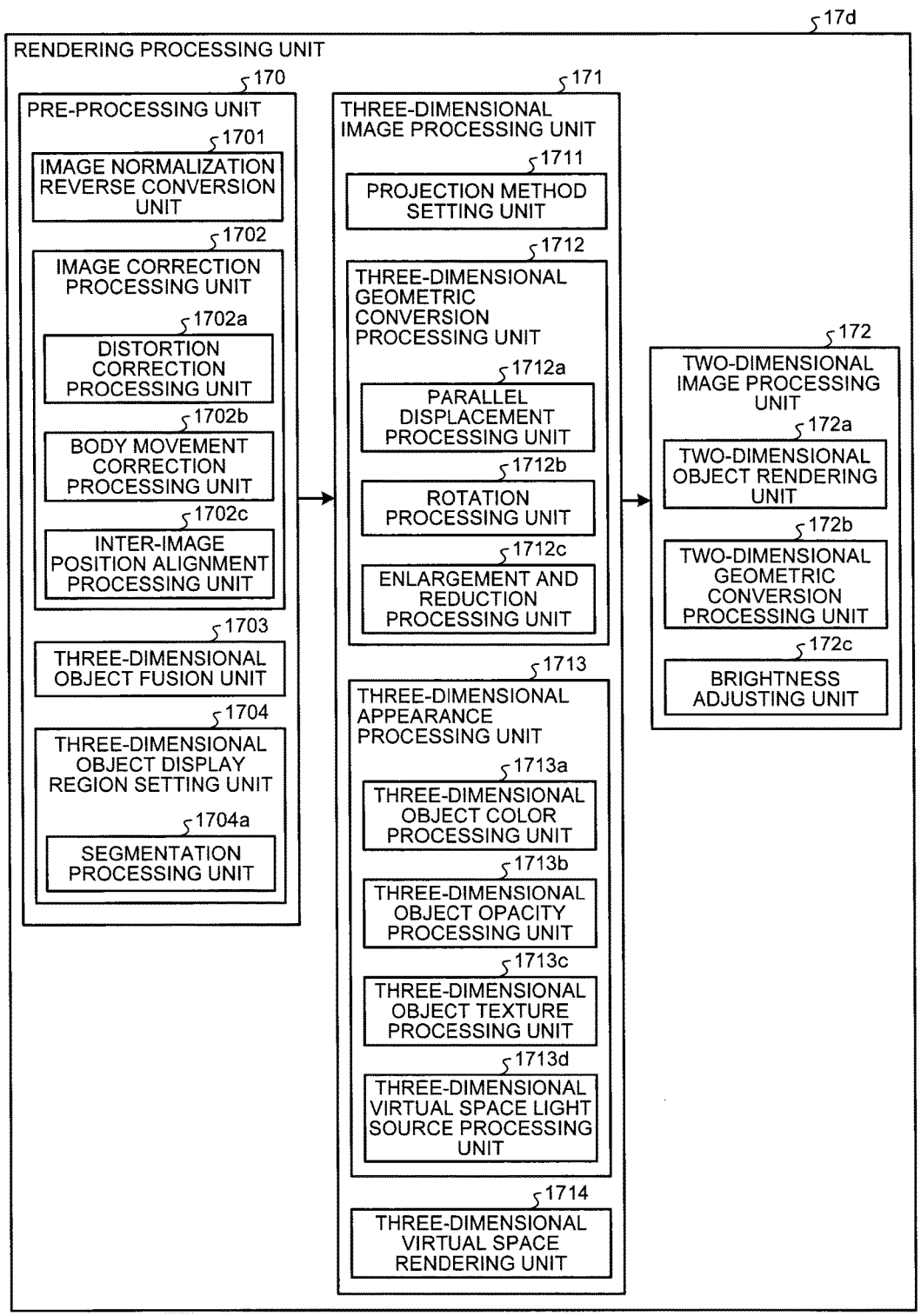
FIG. 3 is a drawing for explaining an exemplary configuration of a rendering processing unit shown in FIG. 2.

Next, the rendering processing unit 17d shown in FIG. 2 will be further explained in detail, with reference to FIG. 3. FIG. 3 is a drawing for explaining an exemplary configuration of the rendering processing unit shown in FIG. 2.

As shown in FIG. 3, the rendering processing unit 17d includes a pre-processing unit 170, a three-dimensional image processing unit 171, and a two-dimensional image processing unit 172.

The pre-processing unit 170 is a processing unit that performs various types of pre-processing processes before performing the rendering process on the volume data and includes an image normalization reverse conversion unit 1701, an image correction processing unit 1702, a three-dimensional object fusion unit 1703, and a three-dimensional object display region setting unit 1704.

The image normalization reverse conversion unit 1701 performs a reverse conversion process on the volume data that was three-dimensionally reconstructed by the three-dimensional reconstructing unit 17c from the plurality of stored images. In other words, the image normalization reverse conversion unit 1701 performs the reverse conversion process to put the stored images back into the original images, by using the coefficients stored in correspondence with the stored images. For example, the image normalization reverse conversion unit 1701 puts the stored image (Y) back into the original image (X), by using the coefficients "a" and "b" stored in correspondence with each of the stored images. As a result, the image normalization reverse conversion unit 1701 reversely converts the volume data based on the stored images reconstructed by the three-dimensional reconstructing unit 17c into the volume data based on the original images (the volume data generated by the image reconstructing unit 14b).

The image correction processing unit 1702 is a processing unit that performs an image correction process, when two types of volume data are processed as one piece of volume data and includes, as shown in FIG. 3, a distortion correction processing unit 1702a, a body movement correction processing unit 1702b, and an inter-image position alignment processing unit 1702c. For example, when volume data of a PET image and volume data of an X-ray CT image that are generated by a PET-CT apparatus are to be processed as one piece of volume data, the image correction processing unit 1702 performs an image correction process. As another example, when volume data of a T1-weighted image and volume data of a T2-weighted image that are generated by an MRI apparatus are to be processed as one piece of volume data, the image correction processing unit 1702 performs an image correction process.

First, for each piece of volume data, the distortion correction processing unit 1702a corrects a distortion in the data caused by acquiring conditions used during an image taking process performed by the image taking unit 14a. Further, the body movement correction processing unit 1702b corrects movements caused by body movements of the subject that occurred during a data acquisition period used for generating each piece of volume data. The inter-image position alignment processing unit 1702c performs a position alignment (registration) process that uses, for example, a cross-correlation method, on two pieces of volume data on which the correction processes have been performed by the distortion correction processing unit 1702a and the body movement correction processing unit 1702b.

The three-dimensional object fusion unit 1703 fuses together the plurality of pieces of volume data on which the position alignment process has been performed by the inter-image position alignment processing unit 1702c. The processes performed by the image correction processing unit 1702 and the three-dimensional object fusion unit 1703 are omitted if the rendering process is performed on a single piece of volume data.

The three-dimensional object display region setting unit 1704 is a processing unit that sets a display region corresponding to a display target organ specified by the operator and includes a segmentation processing unit 1704a. The segmentation processing unit 1704a is a processing unit that extracts the organ specified by the operator such as the heart, a lung, a blood vessel, by using, for example, a region growing method based on pixel values (voxel values) of the volume data.

If no display target organ was specified by the operator, the segmentation processing unit 1704a does not perform the segmentation process. As another example, if a plurality of display target organs are specified by the operator, the segmentation processing unit 1704a extracts the corresponding plurality of organs. The process performed by the segmentation processing unit 1704a may be performed again, in response to a fine-adjustment request from the operator who has observed the rendering images.

The three-dimensional image processing unit 171 performs the image processing process, more specifically, the volume rendering process, on the pre-processed volume data processed by the pre-processing unit 170. As processing units that perform the volume rendering process, the three-dimensional image processing unit 171 includes a projection method setting unit 1711, a three-dimensional geometric conversion processing unit 1712, a three-dimensional appearance processing unit 1713, and a three-dimensional virtual space rendering unit 1714.

The projection method setting unit 1711 determines a projection method used for generating the volume rendering images. For example, the projection method setting unit 1711 determines whether the volume rendering process is to be performed by using a parallel projection method or is to be performed by using a perspective projection method. The parallel projection method and the perspective projection method will be explained in detail later.

The three-dimensional geometric conversion processing unit 1712 is a processing unit that determines information used for three-dimensionally and geometrically converting the volume data on which the volume rendering process is performed and includes a parallel displacement processing unit 1712a, a rotation processing unit 1712b, and an enlargement and reduction processing unit 1712c. The parallel displacement processing unit 1712a is a processing unit that, when the viewpoint positions used in the volume rendering process are moved in a parallel displacement, determines a displacement amount by which the volume data should be moved in a parallel displacement. The rotation processing unit 1712b is a processing unit that, when the viewpoint positions used in the volume rendering process are moved in a rotational shift, determines a shift amount by which the volume data should be moved in a rotational shift. The enlargement and reduction processing unit 1712c is a processing unit that, when an enlargement or a reduction of the volume rendering images is requested, determines an enlargement ratio or a reduction ratio of the volume data.

The three-dimensional appearance processing unit 1713 includes a three-dimensional object color processing unit 1713a, a three-dimensional object opacity processing unit 1713b, a three-dimensional object texture processing unit 1713c, and a three-dimensional virtual space light source processing unit 1713d. By using these processing units, the three-dimensional appearance processing unit 1713 performs a process to determine a display state of the volume rendering images to be displayed, according to, for example, a request from an operator of an apparatus at a display-purpose output source.

The three-dimensional object color processing unit 1713a is a processing unit that determines the colors applied to the regions resulting from the segmentation process within the volume data. The three-dimensional object opacity processing unit 1713b is a processing unit that determines "opacity" of each of the voxels constituting the regions resulting from the segmentation process within the volume data. A region positioned behind a region of which the opacity is set to "100%" in the volume data will not be rendered in the volume rendering images. As another example, a region of which the opacity is set to "0%" in the volume data will not be rendered in volume rendering images.

The three-dimensional object texture processing unit 1713c is a processing unit that adjusts the texture that is used when each of the regions is rendered, by determining the texture of each of the regions resulting from the segmentation process within the volume data. The three-dimensional virtual space light source processing unit 1713d is a processing unit that determines a position of a virtual light source to be placed in a three-dimensional virtual space and a type of the light source, when the volume rendering process is performed on the volume data. Examples of types of the virtual light source include a light source that radiates parallel light beams from an infinite distance and a light source that radiates radial light beams from a viewpoint.

Based on the various types of information determined by the projection method setting unit 1711, the three-dimensional geometric conversion processing unit 1712, and the three-dimensional appearance processing unit 1713, the three-dimensional virtual space rendering unit 1714 performs the volume rendering process on the volume data. For example, by performing the volume rendering process on the volume data, the three-dimensional virtual space rendering unit 1714 generates nine volume rendering images obtained by shifting the viewpoint positions by a predetermined parallax angle, as explained later.

The three-dimensional virtual space rendering unit 1714 has a function of, not only performing the volume rendering process, but also reconstructing an Multi Planar Reconstruction (MPR) image from the volume data by implementing an MPR method. In addition, the three-dimensional virtual space rendering unit 1714 also has a function of performing a "curved MPR" and a function of performing an "intensity projection".

The volume rendering images generated by the three-dimensional image processing unit 171 from the volume data are each used as an underlay. By superimposing an overlay in which the various types of information (a scale mark, the patient's name, tested items, and the like) are rendered onto the underlay images, output-purpose two-dimensional images are obtained. The two-dimensional image processing unit 172 is a processing unit that generates the output-purpose two-dimensional images by performing an image processing process on the overlay and underlay images. As shown in FIG. 3, the two-dimensional image processing unit 172 includes a two-dimensional object rendering unit 172a, a two-dimensional geometric conversion processing unit 172b, and a brightness adjusting unit 172c.

The two-dimensional object rendering unit 172a is a processing unit that renders the various types of information rendered in the overlay. The two-dimensional geometric conversion processing unit 172b is a processing unit that performs a parallel displacement process or a rotational shift process on the positions of the various types of information rendered in the overlay and applies an enlargement process or a reduction process on the various types of information rendered in the overlay.

The brightness adjusting unit 172c is a processing unit that adjusts brightness levels of the overlay and underlay images, according to parameters used for the image processing process such as the gradation of a monitor at an output destination, a Window Width (WW), and a Window Level (WL).

Further, the processing results of the two-dimensional image processing unit 172 are displayed by the display unit 13, under the control of the display controlling unit 11a. Also, after processes are performed thereon by the stereoscopic image transferring unit 17e (explained later), the processing results of the two-dimensional image processing unit 172 are transferred to an external apparatus via the communicating unit 18. The processes performed by the two-dimensional image processing unit 172 may be performed while being shared between the output source and the output destination.

In the medical image processing system shown in FIG. 1, the specifications of the monitor connected to a display-purpose output target apparatus and the monitor connected to an apparatus that reads data from a storing-purpose output target apparatus and displays the read data are not necessarily the same as the specifications of the monitor connected to an output source apparatus. In this situation, the "specifications of a monitor" refers to, more specifically, the specifications related to stereoscopic views.

In other words, commonly-used general-purpose monitors that are currently most popularly used are configured to display two-dimensional images in a two-dimensional manner and are not capable of stereoscopically displaying two-dimensional images. If a viewer wishes to have a stereoscopic view on a general-purpose monitor, the apparatus that outputs images to the general-purpose monitor needs to have two-eye parallax images displayed side by side that enable the viewer to have a stereoscopic view by using a parallel view method or a cross-eyed view method. Alternatively, the apparatus that outputs images to a general-purpose monitor needs to have images displayed that enable the viewer to have a stereoscopic view by, for example, using an anaglyphic method that requires glasses having red cellophane attached to the left-eye part thereof and blue cellophane attached to the right-eye part thereof.

As other examples, such monitors are also known that enable the viewer to have a stereoscopic view (stereoscopic display apparatuses or stereoscopic display monitors) with a plurality of parallax images that were taken from a plurality of viewpoints and have mutually-different parallax angles. An example of such a stereoscopic display apparatus is configured to enable the viewer to have a stereoscopic view with two parallax images (two-eye parallax images or binocular parallax images), by using an exclusive-use device such as stereoscopic glasses.

Figure 4A:
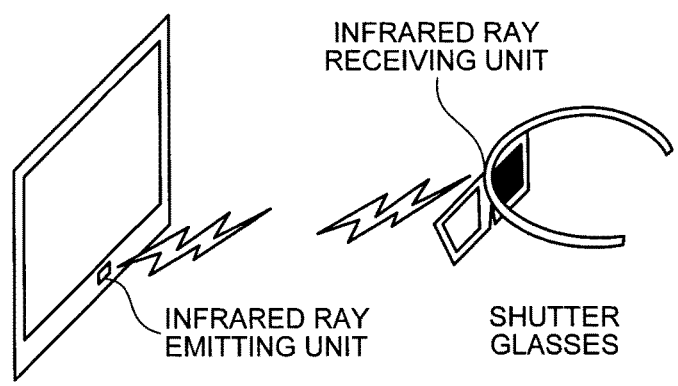
FIG. 4A is a first drawing for explaining an example of a stereoscopic display apparatus that realizes a stereoscopic display by using two-eye parallax images.
Figure 4B:
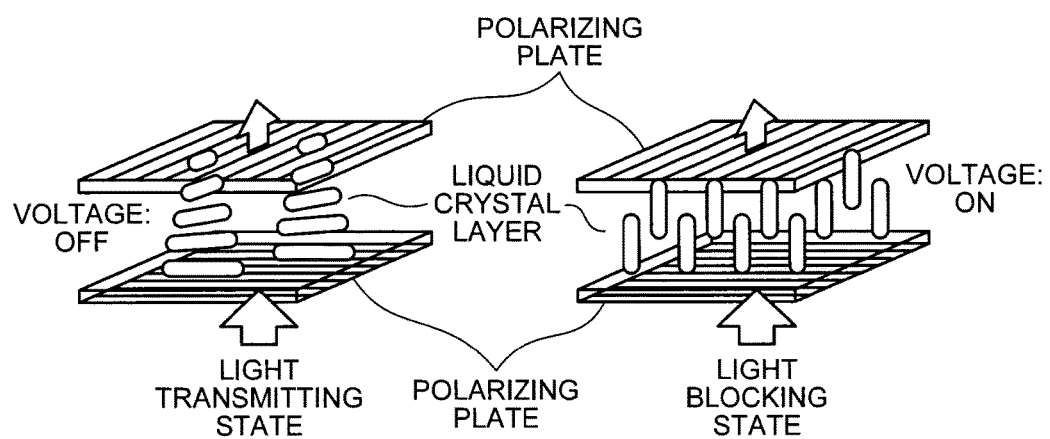
FIG. 4B is a second drawing for explaining the example of the stereoscopic display apparatus that realizes the stereoscopic display by using the two-eye parallax images.

FIGS. 4A and 4B are drawings for explaining an example of a stereoscopic display apparatus that realizes a stereoscopic display by using two-eye parallax images. The example shown in FIGS. 4A and 4B represents a stereoscopic display apparatus that realizes a stereoscopic display by using a shutter method and uses shutter glasses as the stereoscopic glasses worn by the viewer who looks at the monitor. The stereoscopic display apparatus is configured to alternately emit two-eye parallax images from the monitor. For example, the monitor shown in FIG. 4A emits images to be viewed by the left eye (hereinafter, "left-eye images") and images to be viewed by the right eye (hereinafter, "right-eye images") alternately at 120 Hz. In this situation, as shown in FIG. 4A, the monitor is provided with an infrared ray emitting unit, which controls emissions of infrared rays in synchronization with the timing with which the images are switched.

The infrared rays emitted from the infrared ray emitting unit are received by an infrared ray receiving unit of the shutter glasses shown in FIG. 4A. Each of the left and right frames of the shutter glasses has a shutter attached thereto, so that the shutter glasses are able to alternately switch between a light transmitting state and a light blocking state, for each of the left and the right shutters in synchronization with the timing with which the infrared rays are received by the infrared ray receiving unit. In the following sections, the process to switch between the light transmitting state and the light blocking state of the shutters will be explained.

As shown in FIG. 4B, each of the shutters includes an entering-side polarizing plate and an exiting-side polarizing plate and further includes a liquid crystal layer between the entering-side polarizing plate and the exiting-side polarizing plate. The entering-side polarizing plate and the exiting-side polarizing plate are positioned orthogonal to each other as shown in FIG. 4B. In this situation, as shown in FIG. 4B, while the voltage is not applied ("OFF"), the light that has passed through the entering-side polarizing plate is rotated by 90 degrees due to an action of the liquid crystal layer and transmits through the exiting-side polarizing plate. In other words, the shutter is in the light transmitting state while the voltage is not being applied.

On the contrary, as shown in FIG. 4B, while the voltage is being applied ("ON"), because the polarization rotation action of the liquid crystal molecules in the liquid crystal layer is lost, the light that has passed through the entering-side polarizing plate is blocked by the exiting-side polarizing plate. In other words, the shutter is in the light blocking state while the voltage is being applied.

In this arrangement, for example, the infrared ray emitting unit emits infrared rays during the time period when a left-eye image is being displayed on the monitor. The infrared ray receiving unit applies no voltage to the left-eye shutter and applies a voltage to the right-eye shutter, during the time period when receiving the infrared rays. As a result, as shown in FIG. 4A, the right-eye shutter is in the light blocking state, whereas the left-eye shutter is in the light transmitting state, so that the left-eye image goes into the left eye of the viewer. On the contrary, the infrared ray emitting unit stops emitting infrared rays during the time period when a right-eye image is being displayed on the monitor. The infrared ray receiving unit applies no voltage to the right-eye shutter and applies a voltage to the left-eye shutter, during the time period when receiving no infrared rays. As a result, the left-eye shutter is in the light blocking state, whereas the right-eye shutter is in the light transmitting state, so that the right-eye image goes into the right eye of the viewer. As explained here, the stereoscopic display apparatus shown in FIGS. 4A and 4B displays the images that enable the viewer to have a stereoscopic view by switching the images displayed by the monitor and the state of the shutters in conjunction with one another.

Further, examples of stereoscopic display apparatuses that were put in practical use in recent years include an apparatus that enables the viewer with naked eyes to have a stereoscopic view of multiple-eye parallax images such as nine parallax images (nine-eye parallax images) by using a light beam controller such as a lenticular lens. Such a stereoscopic display apparatus is configured to enable the viewer to have a stereoscopic view using a binocular parallax and further enables the viewer to have a stereoscopic view using a motion parallax, by which the viewed pictures also change in accordance with shifting of the viewpoints of the viewer.

Figure 5:
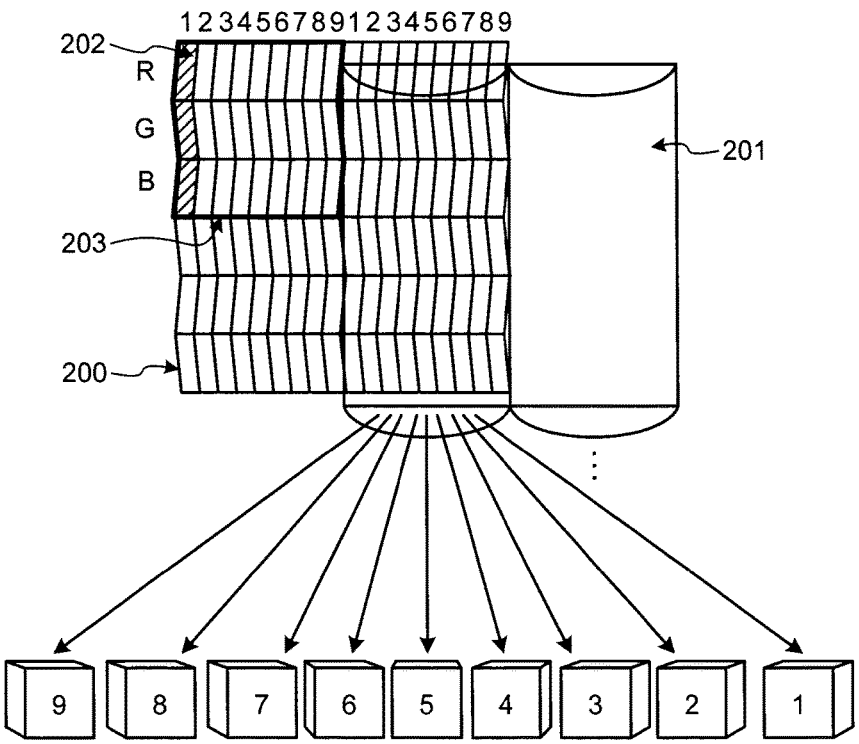
FIG. 5 is a drawing for explaining an example of a stereoscopic display apparatus that realizes a stereoscopic display by using nine-eye parallax images.

FIG. 5 is a drawing for explaining an example of a stereoscopic display apparatus that realizes a stereoscopic display by using nine-eye parallax images. The stereoscopic display apparatus shown in FIG. 5 is configured so that a light beam controller is disposed to the front of a flat-shaped display surface 200 such as a liquid crystal panel. For example, the stereoscopic display apparatus shown in FIG. 5 is configured so that, as the light beam controller, a vertical lenticular sheet 201 of which the optical openings extend in vertical directions is pasted onto the front of the display surface 200. In the example shown in FIG. 5, the vertical lenticular sheet 201 is pasted in such a manner that the convex parts thereof are positioned to the front. However, the vertical lenticular sheet 201 may be pasted in such a manner that the convex parts thereof face the display surface 200.

As shown in FIG. 5, on the display surface 200, pixels 202 are arranged in a matrix formation, each of the pixels 202 having a length-width ratio of 3:1 and having three subpixels for red (R), green (G), and blue (B) arranged in the lengthwise direction. The stereoscopic display apparatus shown in FIG. 5 is configured to convert nine-eye parallax images made up of nine images into intermediate images that are arranged in a predetermined format (e.g., a tiled formation) and outputs the conversion result to the display surface 200. In other words, the stereoscopic display apparatus shown in FIG. 5 outputs nine pixels in mutually the same position in the nine-eye parallax images, while assigning those pixels to nine columns of the pixels 202, respectively. The nine columns of pixels 202 form, as shown in FIG. 5, a unit pixel group 203 that simultaneously displays nine images having mutually-different parallax angles.

The nine-eye parallax images that are simultaneously output as the unit pixel group 203 from the display surface 200 are emitted as parallel beams by a Light Emitting Diode (LED) backlight and are further emitted in multiple directions by the vertical lenticular sheet 201. Because the light beams of the pixels in the nine-eye parallax images are emitted in the multiple directions, the light beams entering the right eye and the left eye of the viewer change in conjunction with the position of the viewer (the position of the viewpoint). In other words, depending on the angle at which the viewer views the image, the parallax angles of the parallax image entering the right eye and the parallax image entering the left eye vary. As a result, the viewer is able to have a stereoscopic view of the target of an image-taking process (hereinafter, "image-taking target") at each of the nine positions shown in FIG. 5, for example. Further, for example, the viewer is able to have a stereoscopic view at the position "5" shown in FIG. 5 while facing the image-taking target straight on and is able to have a stereoscopic view at each of the positions other than the position "5" shown in FIG. 5 while the direction of the image-taking target is varied.

In the following sections, a general-purpose monitor that is not capable of providing stereoscopic views may be referred to as a "non-parallax monitor", whereas the stereoscopic display apparatus explained with reference to FIG. 4 may be referred to as a "two-eye parallax monitor", while the stereoscopic display apparatus explained with reference to FIG. 5 may be referred to as a "nine-eye parallax monitor". In this situation, the "two-eye parallax monitor" and the "nine-eye parallax monitor" can be defined as below, based on the explanations above. The "two-eye parallax monitor" is a display unit configured to display images for realizing a stereoscopic view corresponding to one viewing direction. In contrast, the "nine-eye parallax monitor" is a display unit configured to display images for realizing a stereoscopic view corresponding to a plurality of viewing directions and is an apparatus configured in such a manner that the pair of images that is for realizing the stereoscopic view and is visible to the viewer is changed according to each of the viewing directions.

When the display unit 13 connected to the medical image diagnosis apparatus 10 is a "nine-eye parallax monitor", the rendering processing unit 17d generates nine-eye-parallax volume rendering images in response to a request from the operator of the medical image diagnosis apparatus 10. Further, the controlling unit 11 converts the nine-eye-parallax volume rendering images into, for example, intermediate images arranged in a tiled formation and causes the display unit 13 to display the conversion result. As a result, the operator of the medical image diagnosis apparatus 10 is able to have a stereoscopic view of the volume data resulting from the image taking process.

As another example, let us discuss a situation where the monitor connected to the client terminal device 20 is a "nine-eye parallax monitor". In such a situation, by receiving the nine-eye-parallax volume rendering images generated by the medical image diagnosis apparatus 10, the client terminal device 20 is able to display stereoscopic images that enable the operator of the client terminal device 20 to have a stereoscopic view, in the same manner as with the operator of the medical image diagnosis apparatus 10. However, for example, if the optimal parallax angle that enables the operator of the client terminal device 20 to have the stereoscopic view is different from the optimal parallax angle that enables the operator of the medical image diagnosis apparatus 10 to have the stereoscopic view, the client terminal device 20 is not able to display stereoscopic images that enable the operator thereof to have a stereoscopic view in the same manner as with the operator of the medical image diagnosis apparatus 10.

As another example, if the monitor connected to the client terminal device 21 is a "two-eye parallax monitor", even if the client terminal device 21 has received the nine-eye parallax images, the client terminal device 21 is not able to display two-eye parallax images. In yet another example, if the monitor connected to the client terminal device 22 is a "non-parallax monitor", even if the client terminal device 22 has received the nine-eye parallax images, the client terminal device 22 is only able to display the parallax images two-dimensionally. Further, depending on the stereoscopic methods used by the monitors connected to the workstation 30 and the image storing apparatus 31, the same problem as described above occurs. Also, when the display unit 13 connected to the medical image diagnosis apparatus 10 is a "two-eye parallax monitor" or a "non-parallax monitor", the same problem as described above occurs.

To cope with these situations, the medical image diagnosis apparatus 10 according to the first embodiment is configured to perform the processes described below, to realize a stereoscopic view of three-dimensional medical images, in compliance with each stereoscopic method.

Specifically, from the volume data generated by the medical image diagnosis apparatus 10, it is possible to generate volume rendering images (parallax images) having an arbitrary parallax angle and an arbitrary parallax number. For this reason, the medical image diagnosis apparatus 10 generates rendering images that are able to realize a stereoscopic view on the display unit connected to the output target apparatus serving as an output target, by performing a rendering process on the volume data based on information related to stereoscopic functions of the display unit connected to the output target apparatus serving as the output target. In other words, based on the information related to the stereoscopic functions of the display unit connected to the output target apparatus serving as the output target, the medical image diagnosis apparatus 10 determines a parallax image number (a parallax number) of the images that are for realizing a stereoscopic view and are to be displayed by the display unit and generates rendering images corresponding to the determined parallax image number (the determined parallax number) by performing the rendering process on the volume data that represents the three-dimensional medical images. To explain an example, the medical image diagnosis apparatus 10 receives the information related to the stereoscopic functions of the display unit connected to the output target apparatus serving as an output target. For example, the medical image diagnosis apparatus 10 receives a parallax angle and a parallax number as stereoscopic attributes of the display unit connected to the group of client terminal devices 2 serving as display-purpose output targets. After that, based on the received information related to the stereoscopic functions, the medical image diagnosis apparatus 10 determines a parallax angle and a parallax number and generates rendering images that are able to realize a stereoscopic view on the display unit connected to the output target apparatus serving as the output target, by performing a rendering process on the volume data. In other words, the medical image diagnosis apparatus 10 generates the rendering images corresponding to the parallax number of the display unit connected to the group of client terminal devices 2. For example, when determining the parallax image number (the parallax number), the medical image diagnosis apparatus 10 changes the parallax image number (the parallax number), in compliance with an output target apparatus connected to a display unit (a two-eye parallax monitor) configured to display images for realizing a stereoscopic view corresponding to one viewing direction and with an output target apparatus connected to a display unit (a nine-eye parallax monitor) configured to display images for realizing a stereoscopic view corresponding to a plurality of viewing directions.

After that, the medical image diagnosis apparatus 10 outputs the rendering images that were generated in the rendering process and that correspond to the parallax image number, to the output target apparatus, as the images that are for realizing the stereoscopic view and are to be simultaneously displayed by the display unit. For example, the medical image diagnosis apparatus 10 transfers the rendering images generated in the rendering process to the client terminal device 21 serving as a display-purpose output target.

In other words, the medical image diagnosis apparatus 10 stores the volume data representing the three-dimensional medical images into the image storage unit 16 serving as a storage apparatus. Further, the medical image diagnosis apparatus 10 generates a group of rendering images including the pair of images that is for realizing the stereoscopic view and corresponds to the plurality of viewing directions, by performing a rendering process on the volume data stored in the image storage unit 16. After that, the display unit 13 of the medical image diagnosis apparatus 10 and the display unit connected to the output target apparatus serving as an output target simultaneously display the pair of images that is for realizing the stereoscopic view and corresponds to the plurality of viewing directions, based on the group of rendering images.

Further, the medical image diagnosis apparatus 10 receives a request for changing the rendering condition for the volume data. For example, the medical image diagnosis apparatus 10 receives a rendering condition change request from the operator of the client terminal device 20 serving as a display-purpose output target. In another example, the medical image diagnosis apparatus 10 receives a rendering condition change request from the operator thereof. After that, the medical image diagnosis apparatus 10 performs a re-rendering process on the volume data, based on the received change request.

After that, the medical image diagnosis apparatus 10 outputs the rendering images generated in the re-rendering process to the output target apparatus. For example, the medical image diagnosis apparatus 10 transfers the rendering images generated in the re-rendering process to the client terminal device 20 serving as a display-purpose output target.

In the first embodiment, based on the information received by the transfer destination operation input unit 18a and the transfer destination apparatus stereoscopic condition input unit 18b, the processes described above are performed by the rendering processing unit 17d, the stereoscopic image transferring unit 17e, and the output unit 18c working in collaboration with one another.

Next, the technical terms used herein will be explained more specifically. The term "stereoscopic images" refers to a group of images that is for realizing a stereoscopic view and has been generated by performing a volume rendering process on volume data. The term "parallax image" refers to each of the images constituting the "stereoscopic images". In other words, the "stereoscopic images" are made up of a plurality of "parallax images" having mutually-different "parallax angles". The term "parallax number" refers to the number of "parallax images" required to be viewed as a stereoscopic view on a stereoscopic display monitor. The term "parallax angle" refers to the angle determined by the intervals between the viewpoint positions and the position of the volume data that are set to generate the "stereoscopic images". Further, the term "nine-eye parallax images" used herein refers to "stereoscopic images" that are made up of nine "parallax images". The term "two-eye parallax images" used herein refers to "stereoscopic images" that are made up of two "parallax images".

Figure 6:
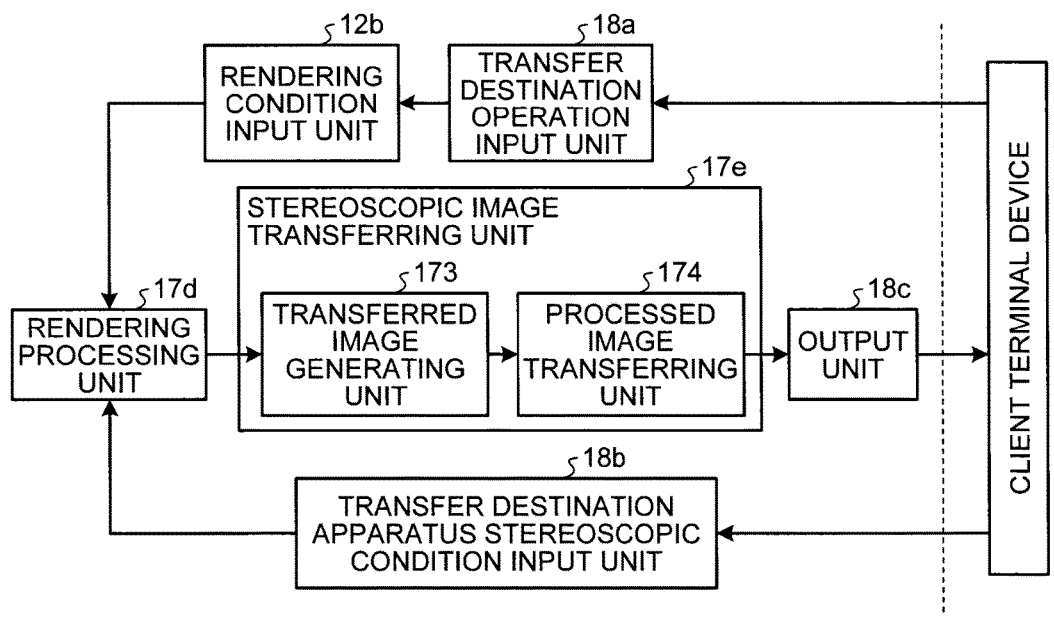
FIG. 6 is a block diagram for explaining processes performed by the rendering processing unit, a stereoscopic image transferring unit, and an output unit according to the first embodiment.

FIG. 6 is a block diagram for explaining processes performed by the rendering processing unit, the stereoscopic image transferring unit, and the output unit according to the first embodiment. Although not shown in FIG. 6, the processes performed by the rendering processing unit 17d, the stereoscopic image transferring unit 17e, and the output unit 18c are performed under the control of the controlling unit 11.

The rendering processing unit 17d according to the first embodiment shown in FIG. 6 performs a volume rendering process, based on information received from an apparatus serving as a display-purpose output target by the transfer destination operation input unit 18a and the transfer destination apparatus stereoscopic condition input unit 18b included in the communicating unit 18.

Figures 7A, 7B, 7C, 8:
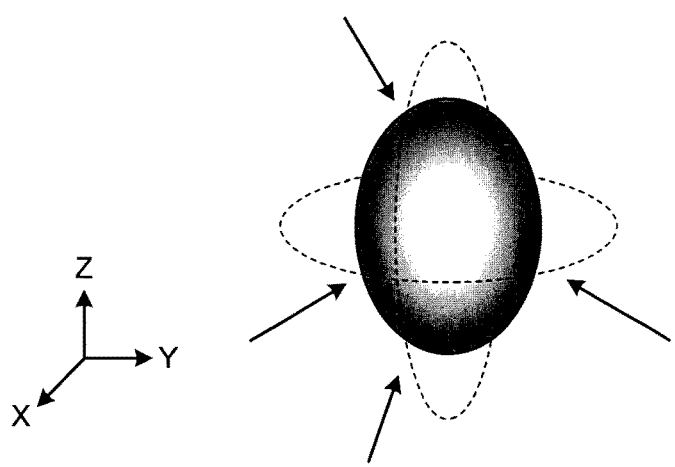
FIG. 7A is a first drawing for explaining an example of stereoscopic attributes.
FIG. 7B is a second drawing for explaining another example of the stereoscopic attributes.
FIG. 7C is a third drawing for explaining yet another example of the stereoscopic attributes.
FIG. 8 is a drawing for explaining an example of an operation event.

The transfer destination apparatus stereoscopic condition input unit 18b receives information related to the stereoscopic functions (stereoscopic attributes) of a display unit (a monitor) connected to the apparatus serving as a display-purpose output apparatus. FIGS. 7A, 7B, and 7C are drawings for explaining examples of the stereoscopic attributes.

For example, as shown in FIG. 7A, the transfer destination apparatus stereoscopic condition input unit 18b receives "parallax number: nine-eye parallax" indicating a "nine-eye parallax monitor", as a stereoscopic attribute of the monitor connected to the client terminal device 20. Further, as shown in FIG. 7A, the transfer destination apparatus stereoscopic condition input unit 18b receives a stereoscopic attribute indicating that the parallax angle of the nine-eye parallax images that are normally observed by the operator of the client terminal device 20 is "1 degree".

In another example, as shown in FIG. 7B, the transfer destination apparatus stereoscopic condition input unit 18b receives "parallax number: two-eye parallax" indicating a "two-eye parallax monitor", as a stereoscopic attribute of the monitor connected to the client terminal device 21. Further, as shown in FIG. 7B, the transfer destination apparatus stereoscopic condition input unit 18b receives a stereoscopic attribute indicating that the parallax angle of the two-eye parallax images that are normally observed by the operator of the client terminal device 21 is "4 degrees".

In yet another example, as shown in FIG. 7C, the transfer destination apparatus stereoscopic condition input unit 18b receives "parallax number: no parallax" indicating a "non-parallax monitor", as a stereoscopic attribute of the monitor connected to the client terminal device 22.

The stereoscopic attributes do not necessarily have to be received from an apparatus serving as a display-purpose output target when a stereoscopic image viewing request is received from the apparatus. For example, an arrangement is acceptable in which the medical image diagnosis apparatus 10 is configured to store therein, in advance, the stereoscopic attributes of the display units of the apparatuses that can be connected thereto. Further, another arrangement is acceptable in which the parallax number used as a stereoscopic attribute is automatically obtained by the medical image diagnosis apparatus 10 from an apparatus serving as a display-purpose output target, by receiving the specifications of the monitor. With either one of the arrangements, the stereoscopic attributes of the apparatus serving as a display-purpose output target are transferred to the rendering processing unit 17d via the controlling unit 11. Further, the stereoscopic attributes used in the process of determining the parallax image number (the parallax number) do not necessarily have to be obtained through the communication, but may be stored into the medical image diagnosis apparatus 10, in advance, through an input via a storage medium or a manual input by the operator, for example.

Returning to the description of FIG. 6, the rendering condition input unit 12b receives a rendering condition related to the volume rendering process, from the operator of the medical image diagnosis apparatus 10 and transfers the received rendering condition to the rendering processing unit 17d. Further, the rendering condition input unit 12b receives a rendering condition received by the transfer destination operation input unit 18a and transfers the received information to the rendering processing unit 17d. More specifically, the transfer destination operation input unit 18a receives the contents of an operation event such as a request for changing the rendering condition related to the volume rendering process that was input by the operator of the client terminal device 20. FIG. 8 is a drawing for explaining an example of the operation event.

For example, as shown in FIG. 8, the transfer destination operation input unit 18a receives, as an operation event input by the operator of the client terminal device 20, a request for changing the viewpoint positions that are used when performing the volume rendering process, from the client terminal device 20. In this situation, in the example shown in FIG. 8, the operator is searching for viewpoint positions from which he/she wishes to view the images, by using a mouse or the like to apply a rotational shift to the volume rendering images, while the client terminal device is displaying, on the monitor, the volume rendering images corresponding to a plurality of viewpoints based on the volume data. As a result of the search, as shown in FIG. 8, the operator of the client terminal device 20 makes a request for a rotational shift of the viewpoint positions on an X-Y plane and/or a request for a rotational shift of the viewpoint positions on an X-Z plane. Other examples of operation events include a request for a parallel displacement of the viewpoint positions, a request for changing the projection method, a request for changing the parallax angle, and a request for changing the parallax number.

Figure 9:
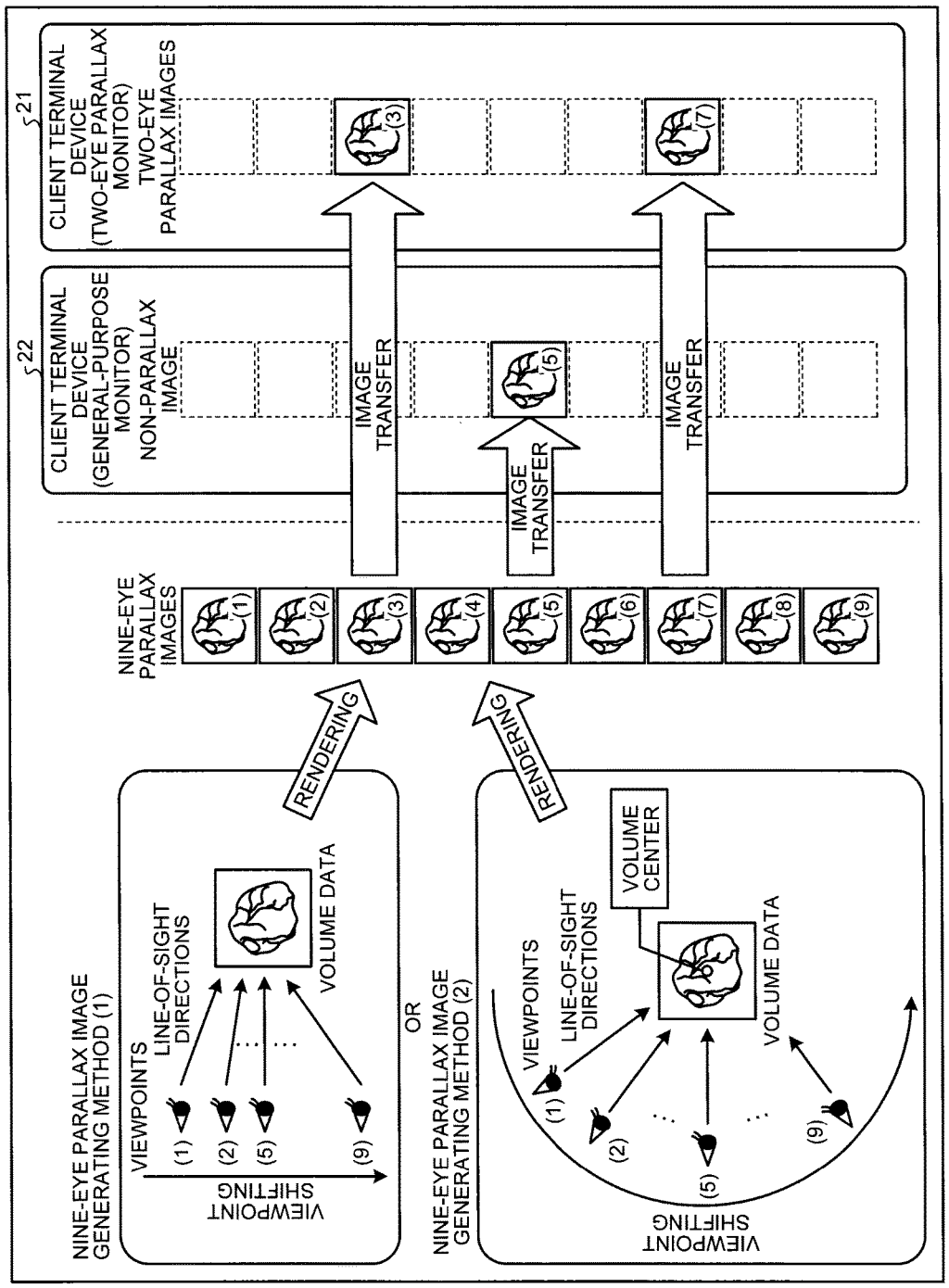
FIG. 9 is a drawing for explaining examples of processes performed by the rendering processing unit and the stereoscopic image transferring unit according to the first embodiment.

First, the rendering processing unit 17d generates stereoscopic images that match the stereoscopic attributes of the display unit 13 of the medical image diagnosis apparatus 10, based on the rendering condition received from the rendering condition input unit 12b or the rendering condition that is initially set. FIG. 9 is a drawing for explaining examples of processes performed by the rendering processing unit and the stereoscopic image transferring unit according to the first embodiment.

For example, let us discuss a situation in which, as shown in "nine-eye parallax image generating method (1)" in FIG. 9, the rendering processing unit 17d receives, as a rendering condition, the parallel projection method and further receives viewpoint position (5) used as a reference point and a parallax angle "1 degree". In that situation, the rendering processing unit 17d uses the parallel projection method and generates nine nine-eye parallax images in which the parallax angles (the angles between the line-of-sight directions) are different by 1 degree each, by moving the viewpoint position to positions (1) to (9) in the manner of a parallel displacement, so that the parallax angles are mutually different by 1 degree. When implementing the parallel projection method, the rendering processing unit 17d sets a light source that radiates parallel light beams from an infinite distance along the line-of-sight directions.

As another example, let us discuss a situation in which, as shown in "nine-eye parallax image generating method (2)" in FIG. 9, the rendering processing unit 17d receives, as a rendering condition, the perspective projection method and further receives viewpoint position (5) used as a reference point and a parallax angle "1 degree". In that situation, the rendering processing unit 17d uses the perspective projection method and generates nine nine-eye parallax images in which the parallax angles are different by 1 degree each, by moving the viewpoint position to positions (1) to (9) in the manner of a rotational shift, so that the parallax angles are mutually different by 1 degree while being centered on the center (the gravity point) of the volume data. When implementing the perspective projection method, the rendering processing unit 17d sets, at each of the viewpoints, a point light source or an area light source that three-dimensionally and radially radiates light being centered on the line-of-sight direction. Alternatively, when implementing the perspective projection method, the rendering processing unit 17d may move viewpoints (1) to (9) in the manner of a parallel displacement, according to the rendering condition.

As yet another example, the rendering processing unit 17*d* may perform a volume rendering process while using the parallel projection method and the perspective projection method together, by setting a light source that two-dimensionally and radially radiates light being centered on the line-of-sight direction with respect to the lengthwise direction of the volume rendering image to be displayed and that radiates parallel light beams from an infinite distance along the line-of-sight direction with respect to the widthwise direction of the volume rendering image to be displayed.

In this situation, the rendering processing unit 17*d* temporarily stores the nine volume rendering images, which are the generated nine-eye parallax images for the medical image diagnosis apparatus 10, into the image memory 15, so that the images are displayed by the display unit 13.

After that, the rendering processing unit 17*d* compares the stereoscopic attributes received by the transfer destination apparatus stereoscopic condition input unit 18*b* with the stereoscopic attributes of the medical image diagnosis apparatus 10. In other words, the rendering processing unit 17*d* determines a parallax number based on the stereoscopic attributes received by the transfer destination apparatus stereoscopic condition input unit 18*b* and compares the determined parallax number with the parallax number based on the stereoscopic attributes of the medical image diagnosis apparatus 10. Also, the rendering processing unit 17*d* determines a parallax angle based on the stereoscopic attributes received by the transfer destination apparatus stereoscopic condition input unit 18*b* and compares the determined parallax angle with the parallax angle based on the stereoscopic attributes of the medical image diagnosis apparatus 10. Subsequently, the rendering processing unit 17*d* judges whether such volume rendering images that match the stereoscopic attributes received by the transfer destination apparatus stereoscopic condition input unit 18*b* are present among the already-generated volume rendering images. For example, when nine-eye parallax images have been generated with a parallax angle of "1 degree", the rendering processing unit 17*d* determines that the images match the stereoscopic attributes of the client terminal device 20. As another example, when nine-eye parallax images have been generated with a parallax angle of "1 degree", the rendering processing unit 17*d* determines that the nine-eye parallax images include two images that match the stereoscopic attribute "parallax angle: 4 degrees" of the client terminal device 21. In other words, when determining the parallax number, the rendering processing unit 17*d* changes the parallax number, in compliance with an output target apparatus connected to a two-eye parallax monitor and with an output target apparatus connected to a nine-eye parallax monitor. Further, for example, when nine-eye parallax images have been generated with a parallax angle of "1 degree", the rendering processing unit 17*d* determines that it will be appropriate to select one image corresponding to the stereoscopic attribute "parallax angle: no parallax" of the client terminal device 22, from among the nine-eye parallax images.

On the contrary, if no such volume rendering images that match the stereoscopic attributes received by the transfer destination apparatus stereoscopic condition input unit 18*b* are present among the already-generated volume rendering images, the rendering processing unit 17*d* performs a volume rendering process again in a real-time manner. For example, if the parallax angle in the stereoscopic attributes of the client terminal device 20 is different from the parallax angle of the medical image diagnosis apparatus 10, the rendering processing unit 17*d* re-generates nine-eye parallax images to match the parallax angle of the client terminal device 20. For example, if nine-eye parallax images have been generated with a parallax angle of "1.2 degrees", the rendering processing unit 17*d* re-generates nine-eye parallax images by using a parallax angle of "1 degree".

As another example, if nine-eye parallax images have been generated with a parallax angle of "1.2 degrees", the rendering processing unit 17*d* re-generates two two-eye parallax images having a parallax angle of "4 degrees", because there are no images that match the "parallax angle: 4 degrees" received as a stereoscopic attribute of the client terminal device 21.

After that, the rendering processing unit 17*d* outputs either the already-generated images or the re-generated images to the stereoscopic image transferring unit 17*e*. When such images that match the stereoscopic attributes of the display-purpose output target apparatus are present among the already-generated images, the rendering processing unit 17*d* outputs such images to the stereoscopic image transferring unit 17*e*, after appending a flag thereto, for example, indicating that the images are output-purpose images.

As shown in FIG. 6, the stereoscopic image transferring unit 17*e* includes a transferred image generating unit 173 and a processed image transferring unit 174. The transferred image generating unit 173 generates images to be transferred (transferred images) from the volume rendering images generated by the rendering processing unit 17*d*. For example, based on the flag appended by the rendering processing unit 17*d*, the stereoscopic image transferring unit 17*e* selects such volume rendering images that match the stereoscopic attributes requested by the display-purpose output target apparatus, from among the plurality of parallax images generated by the rendering processing unit 17*d*.

The example shown in FIG. 9 illustrates a situation where such images that match the stereoscopic attributes of display-purpose output target apparatuses are included in the already-generated images. More specifically, as shown in FIG. 9, by referring to the appended flag, the transferred image generating unit 173 selects the volume rendering image corresponding to viewpoint (5) as a transferred image for the client terminal device 22 to which a general-purpose monitor (a non-parallax monitor) is connected. As another example, as shown in FIG. 9, by referring to the appended flag, the transferred image generating unit 173 selects the volume rendering images corresponding to viewpoints (3) and (7) having a parallax angle of "4 degrees", as transferred images for the client terminal device 21 to which a two-eye parallax monitor is connected. As yet another example, the transferred image generating unit 173 selects all of the volume rendering images corresponding to viewpoints (1) to (9), as transferred images that are nine-eye parallax images for the client terminal device 20 to which a nine-eye parallax monitor is connected.

Further, in addition to the transferred image selecting process, the transferred image generating unit 173 performs an image compression process on the volume rendering images. The image compression process performed by the transferred image generating unit 173 may be a lossless compression process or a lossy compression process. More specifically, the transferred image generating unit 173 generates the transferred images by performing the image compression process so as to prevent the transfer speed from being lowered. After that, as shown in FIG. 9, the processed image transferring unit 174 outputs the transferred images selected and generated by the transferred image generating unit 173 to the output unit 18c included in the communicating unit 18, so that the output unit 18c transmits the images to the display-purpose output target apparatus.

As a result, for example, the operator of the client terminal device 20 is able to have a stereoscopic view using a binocular parallax and a motion parallax, on the "nine-eye parallax monitor". As another example, the operator of the client terminal device 21 is able to have a stereoscopic view using a binocular parallax, on the "two-eye parallax monitor". As yet another example, the operator of the client terminal device 22 is able to view the volume rendering image corresponding to the viewpoint used as the reference point, on the "non-parallax monitor". The image that is output and transferred to the client terminal device 22 may be only the volume rendering image corresponding to viewpoint (5) as described above, or may be the volume rendering images corresponding to viewpoints (1) to (9). In the latter situation, the output unit 18c transfers the volume rendering images corresponding to viewpoints (1) to (9) to the client terminal device 22, after appending thereto accompaniment information indicating that the volume rendering images are a group of images to be displayed side by side. Alternatively, the output unit 18c may transfer the volume rendering images corresponding to viewpoints (1) to (9) to the client terminal device 22, after appending thereto accompaniment information indicating that the volume rendering images are a group of images that can be displayed as a moving picture. In that situation, the operator of the client terminal device 22 is able to view the moving picture in which the volume rendering images from the nine mutually-different directions rotate.

In this situation, if the operator of the apparatus serving as a display-purpose output target makes a rendering condition change request, the transfer destination operation input unit 18a transfers the rendering condition change request received from the display-purpose output target apparatus to the rendering condition input unit 12b. For example, as shown in FIG. 8, the transfer destination operation input unit 18a transfers a viewpoint position change request to the rendering condition input unit 12b. In other examples, the transfer destination operation input unit 18a transfers a projection method change request, a display attribute (appearance attribute) change request, a segmentation portion change request, a parallax angle change request, and/or a parallax number change request, to the rendering condition input unit 12b.

When having received a rendering condition change request from the rendering condition input unit 12b, the rendering processing unit 17d performs a re-rendering process on the volume data, based on the changed rendering condition. For example, in response to a viewpoint position change request received from the client terminal device 20, the rendering processing unit 17d changes the viewpoint position used as the reference point and generates nine-eye parallax images. In another example, in response to a parallax angle change request received from the client terminal device 20, the rendering processing unit 17d changes the eight viewpoint positions centered around the viewpoint position used as the reference point and generates nine-eye parallax images.

In yet another example, in response to a parallax number change request received from the client terminal device 20, the rendering processing unit 17d generates two-eye parallax images. In yet another example, in response to a projection method change request received from the client terminal device 20, the rendering processing unit 17d changes from the perspective projection method to the parallel projection method, for example, and generates nine-eye parallax images. In yet another example, in response to a parallax angle change request received from the client terminal device 21, the rendering processing unit 17d generates two-eye parallax images that have, for example, a parallax angle of "3 degrees".

The rendering images that were re-generated in this manner by the rendering processing unit 17d based on the changed rendering condition are output to the stereoscopic image transferring unit 17e. Further, the transferred image generating unit 173 performs an image compression process on the volume rendering images so as to generate transferred images. Subsequently, the processed image transferring unit 174 outputs the transferred images generated by the transferred image generating unit 173 to the output unit 18c included in the communicating unit 18, so that the output unit 18c transmits the images to the display-purpose output target apparatus. When having received a request from the operator of the client terminal device 20 indicating that no stereoscopic view is required, the stereoscopic image transferring unit 17e is able to select, for example, the volume rendering image corresponding to viewpoint (5) as an image to be transferred and outputs the selected image to the output unit 18c. Further, a rendering condition change request may be made by the operator of the medical image diagnosis apparatus 10. In that situation also, the rendering processing unit 17d performs a re-rendering process based on the changed rendering condition and outputs the images to the stereoscopic image transferring unit 17e.

To summarize the explanations above, the stereoscopic images generated in a real-time manner by the rendering processing unit 17d in response to a request from the operator are "multiple-eye parallax images corresponding to one viewpoint" centered around the viewpoint used as a reference point. The rendering processing unit 17d according to the first embodiment selects in a real-time manner or re-generates in a real-time manner the "multiple-eye parallax images corresponding to one viewpoint" that match the stereoscopic attributes or the rendering condition change request of the apparatus serving as the display-purpose output target. In other words, the rendering processing unit 17d according to the first embodiment generates in a real-time manner the images that are for realizing the stereoscopic view and are to be output to the display-purpose output target, by changing the rendering condition set in the medical image diagnosis apparatus 10 so as to match the request from the user.

The apparatuses serving as display-purpose output targets may be not only the group of client terminal devices 2 explained above, but also the group of external apparatuses 3 or the group of client terminal devices 5 of which each member is connectable to the image storing apparatus 31. For example, when the group of client terminal devices 5 is the display-purpose output targets, the transfer destination operation input unit 18a and the transfer destination apparatus stereoscopic condition input unit 18b receive the stereoscopic attributes and the rendering condition change requests via the image storing apparatus 31.

Further, the volume rendering images transferred to the apparatus serving as a display-purpose output target may be not only displayed by the apparatus, but also stored into a cache memory or the like. By storing the volume rendering images, the operator of the display-purpose output target is able to have a stereoscopic view of the volume data serving as a viewed target, at an arbitrary time.

Further, to an output target apparatus having a display unit configured to switch among the images for realizing a stereoscopic view (the stereoscopic images) at predetermined time intervals, the stereoscopic image transferring unit 17e and the output unit 18c may output a group of rendering images for the output target apparatus, while switching among the rendering images in the group at the predetermined time intervals. For example, when transferring two-eye parallax images, the stereoscopic image transferring unit 17e and the output unit 18c may alternately output the two parallax images according to the image switching speed of the two-eye parallax monitor.

The first embodiment is also applicable to a situation where the process of generating the stereoscopic images based on the stereoscopic attributes of the display unit 13 of the medical image diagnosis apparatus 10 and the rendering condition input by the operator of the medical image diagnosis apparatus 10 is not performed. In such a situation, when having received the stereoscopic attributes of the apparatus serving as a display-purpose output target, the medical image diagnosis apparatus 10 determines a parallax number (and a parallax angle) based on the received stereoscopic attributes. After that, the medical image diagnosis apparatus 10 generates rendering images corresponding to the determined parallax number (and the determined parallax angle) and transfers transferred images of the stereoscopic images that were generated. In other words, in that situation, the rendering processing unit 17d does not perform the selecting process.

Figure 10:
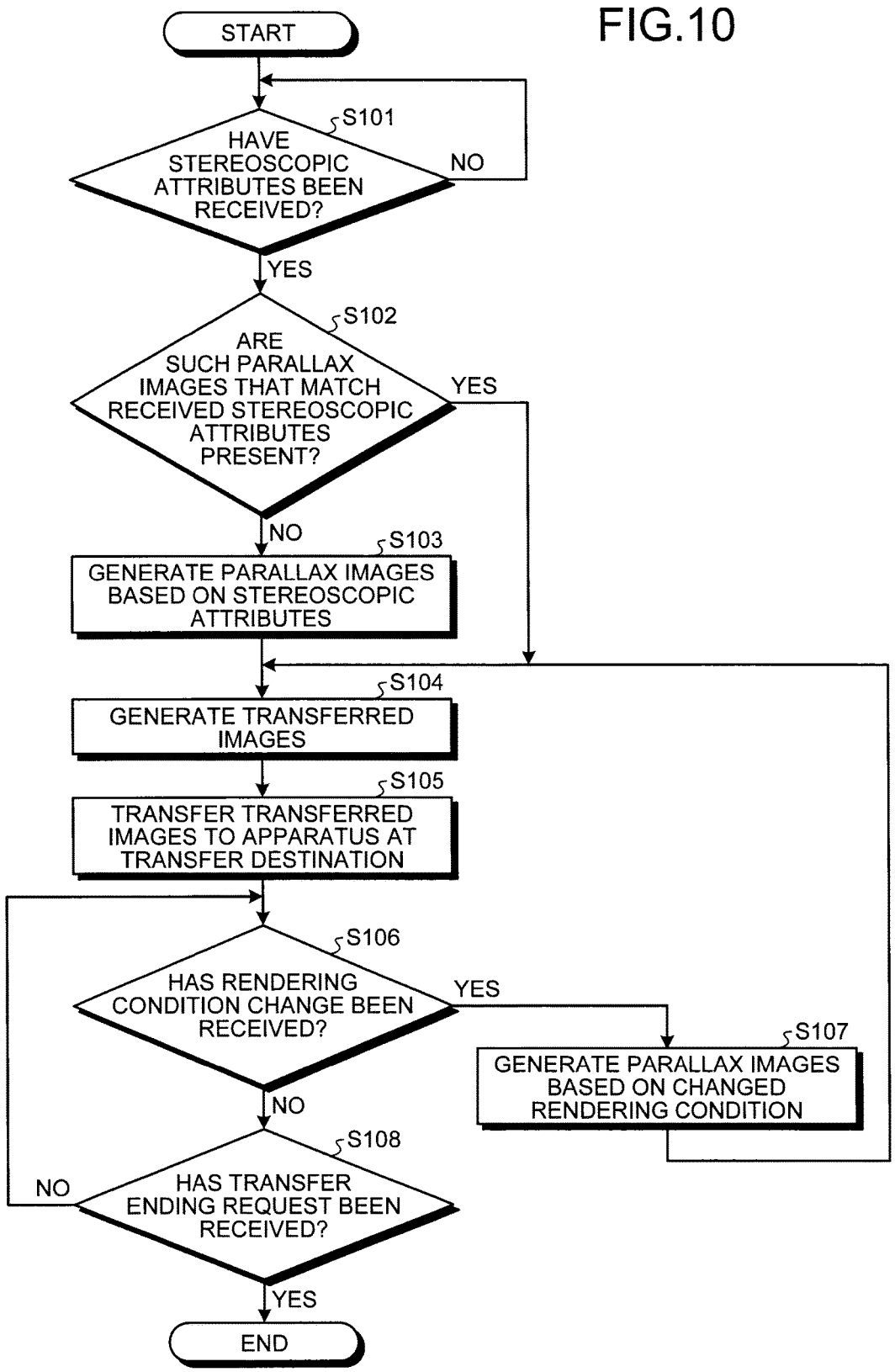
FIG. 10 is a flowchart for explaining a process performed for a display-purpose output target by the medical image diagnosis apparatus according to the first embodiment.

Next, a process performed for a display-purpose output target by the medical image diagnosis apparatus 10 according to the first embodiment will be explained, with reference to FIG. 10. FIG. 10 is a flowchart for explaining the process performed for a display-purpose output target by the medical image diagnosis apparatus according to the first embodiment. In the following sections, a process that is performed after the rendering processing unit 17d has generated the volume rendering images to be output to the medical image diagnosis apparatus 10 will be explained.

As shown in FIG. 10, the medical image diagnosis apparatus 10 according to the first embodiment judges whether the transfer destination apparatus stereoscopic condition input unit 18b has received stereoscopic attributes (step S101). In this situation, if no stereoscopic attributes have been received (step S101: No), the medical image diagnosis apparatus 10 according to the first embodiment goes into a standby state.

On the contrary, if stereoscopic attributes have been received (step S101: Yes), the rendering processing unit 17d judges whether such parallax images that match the received stereoscopic attributes are present among the already-generated volume rendering images (step S102). In this situation, if no such parallax images that match the received stereoscopic attributes are present (step S102: No), the rendering processing unit 17d generates parallax images based on the received stereoscopic attributes (step S103), and the stereoscopic image transferring unit 17e generates transferred images (step S104).

On the contrary, if such parallax images that match the received stereoscopic attributes are present (step S102: Yes), the rendering processing unit 17d notifies the stereoscopic image transferring unit 17e of the parallax images that match the received stereoscopic attributes. The stereoscopic image transferring unit 17e selects the images to be transferred based on the notified information and generates transferred images (step S104).

After that, the output unit 18c transfers the transferred images to the apparatus at a transfer destination (step S105), and the transfer destination operation input unit 18a judges whether a rendering condition change has been received (step S106). In this situation, if a rendering condition change has been received (step S106: Yes), the rendering processing unit 17d generates parallax images based on the changed rendering condition (step S107), and the medical image diagnosis apparatus 10 subsequently performs the processes at step S104 and thereafter.

On the contrary, if no rendering condition change is received (step S106: No), the controlling unit 11 judges whether a transfer ending request has been received (step S108). In this situation, if no transfer ending request is received (step S108: No), the process returns to step S106, where it is judged whether a rendering condition change has been received.

On the contrary, if a transfer ending request has been received (step S108: Yes), the medical image diagnosis apparatus 10 according to the first embodiment ends the process.

The first embodiment may be configured so that the judging process at step S102 is performed by the stereoscopic image transferring unit 17e. Further, the first embodiment is also applicable to a situation where, as explained above, the volume rendering process in compliance with the stereoscopic attributes of the medical image diagnosis apparatus 10 is not performed, but only the volume rendering process in compliance with the stereoscopic attributes of the display-purpose output target and the rendering condition change request made by the operator of the display-purpose output target is performed. In that situation, according to the first embodiment, the judging process at step S102 is omitted, so that after the stereoscopic attributes are received at step S101, the process at step S103 is performed. Further, the first embodiment is also applicable to a situation where the display unit 13 of the medical image diagnosis apparatus 10 is a "non-parallax monitor" or a "two-eye parallax monitor".

As explained above, according to the first embodiment, because it is possible to perform the image generating process and the image output process in compliance with the stereoscopic attributes of the apparatus serving as the display-purpose output target, it is possible to provide the stereoscopic view of the three-dimensional medical images (the volume data) in compliance with each stereoscopic method. For example, according to the first embodiment, it is possible to reproduce, on another apparatus, the stereoscopic effect viewed on the apparatus directly connected to the nine-eye parallax monitor. Thus, on mutually-different apparatuses, it is possible to enable the same viewer to have a stereoscopic view of the volume data with the same stereoscopic effect. In other words, according to the first embodiment, it is possible to maximally utilize the stereoscopic capability of the monitors of the apparatuses serving as the display-purpose output targets.

Second Embodiment

As a second embodiment, an example will be explained in which volume rendering images are displayed in synchronization among a plurality of apparatuses serving as display-purpose output targets.

Figure 11:
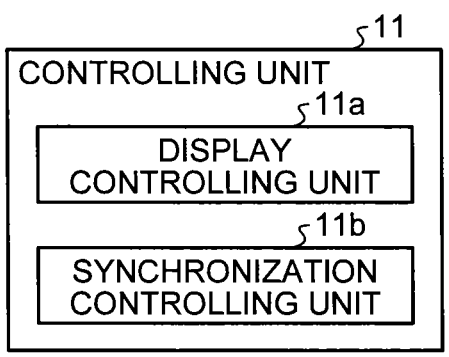
FIG. 11 is a drawing for explaining an exemplary configuration of a controlling unit according to a second embodiment.

FIG. 11 is a drawing for explaining an exemplary configuration of a controlling unit according to the second embodiment. The controlling unit 11 according to the second embodiment further includes a synchronization controlling unit 11b, in addition to the display controlling unit 11a that controls the display of the display unit 13.

More specifically, in the second embodiment, when there are a plurality of apparatuses serving as display-purpose output targets, the rendering processing unit 17d performs a rendering process on the volume data, based on the information related to the stereoscopic functions (the stereoscopic attributes) and the rendering condition for the volume data of each of the monitors (the display units) respectively connected to the plurality of display-purpose output targets, under the control of the synchronization controlling unit 11b. In other words, the rendering processing unit 17d determines a parallax image number (a parallax number) for each of the plurality of display-purpose output target apparatuses, based on the information related to the stereoscopic functions of each of the display units respectively connected to the plurality of display-purpose output target apparatuses. Further, based on the parallax image number (parallax number) and the rendering condition for the volume data of each of the plurality of output target apparatuses, the rendering processing unit 17d performs the rendering process on the volume data. After that, under the control of the synchronization controlling unit 11b, the output unit 18c outputs the rendering images generated by the rendering processing unit 17d for each of the plurality of display-purpose output target apparatuses to the corresponding one of the output target apparatuses, in synchronization among the output target apparatuses.

In this situation, there are various patterns in which a synchronized display is started. In one example, the operator of the client terminal device 20 takes an initiative and wishes to view the same volume data generated by the medical image diagnosis apparatus 10, with the same stereoscopic attributes, at the same time as the operator of the medical image diagnosis apparatus 10. In that situation, the client terminal device 20 transmits a synchronized display request to the communicating unit 18, together with information indicating that the synchronized display target is the medical image diagnosis apparatus 10.

Having been notified of the synchronized display request by the communicating unit 18 via the controlling unit 11, the rendering processing unit 17d generates volume rendering images satisfying "parallax number: 9; parallax angle: 1 degree". The display controlling unit 11a causes the display unit 13 to display the volume rendering images satisfying "parallax number: 9; parallax angle: 1 degree". Further, the stereoscopic image transferring unit 17e and the output unit 18c transmit the volume rendering images satisfying "parallax number: 9; parallax angle: 1 degree", to the client terminal device 20.

In another example, the operator of the client terminal device 21 takes an initiative and wishes to view the same volume data generated by the medical image diagnosis apparatus 10, with mutually-different stereoscopic attributes, at the same time as the operator of the medical image diagnosis apparatus 10. In that situation, the client terminal device 21 transmits a synchronized display request to the communicating unit 18, together with information indicating that the synchronized display target is the medical image diagnosis apparatus 10.

Having been notified of the synchronized display request by the communicating unit 18 via the controlling unit 11, the rendering processing unit 17d generates volume rendering images satisfying "parallax number: 9; parallax angle: 1 degree". The display controlling unit 11a causes the display unit 13 to display the volume rendering images satisfying "parallax number: 9; parallax angle: 1 degree". Further, the rendering processing unit 17d selects two images satisfying "parallax number: 2; parallax angle: 4 degrees" from among the generated volume rendering images, so that the stereoscopic image transferring unit 17e and the output unit 18c transmit the volume rendering images satisfying "parallax number: 2; parallax angle: 4 degrees", to the client terminal device 21. In each of the two patterns described above, another arrangement is acceptable in which the synchronized display request is exercised while the operator of the medical image diagnosis apparatus 10 is taking an initiative.

In yet another example, the operator of the client terminal device 20 takes an initiative and wishes to view the same volume data which is used by the medical image diagnosis apparatus 10 as a rendering target, with mutually-different stereoscopic attributes, at the same time as the operator of the client terminal device 21. In that situation, the client terminal device 20 transmits a synchronized display request to the communicating unit 18, together with information indicating that the synchronized display target is the client terminal device 21.

Having been notified of the synchronized display request by the communicating unit 18 via the controlling unit 11, the rendering processing unit 17d generates volume rendering images satisfying "parallax number: 9; parallax angle: 1 degree". Further, the stereoscopic image transferring unit 17e and the output unit 18c transmit the volume rendering images satisfying "parallax number: 9; parallax angle: 1 degree", to the client terminal device 20. Also, the rendering processing unit 17d selects two images satisfying "parallax number: 2; parallax angle: 4 degrees" from among the generated volume rendering images, so that the stereoscopic image transferring unit 17e and the output unit 18c transmit the volume rendering images satisfying "parallax number: 2; parallax angle: 4 degrees", to the client terminal device 21. In the pattern described above, another arrangement is acceptable in which the synchronized display request is exercised while the operator of the client terminal device 21 is taking an initiative.

As a result of the processes described above, the operator who made the synchronized display request and the operator of the synchronized display target apparatus are each able to have a stereoscopic view of the images obtained by performing the volume rendering process from the same viewpoint positions on the same volume data, in compliance with the stereoscopic specifications of the display unit being used by the operator.

Further, when performing a synchronized display, the synchronization controlling unit 11b exercises control so that the rendering processing unit 17d performs the volume rendering process, based on the rendering condition requested by the operator who has made the synchronized display request. For example, the operator of the client terminal device 20 who has made a synchronized display request selects a rendering condition for generating volume rendering images that he/she wishes to view. The rendering condition may be, for example, attribute values selected from various types of conditions such as viewpoint positions, display attributes (appearance attributes), a projection method, and segmentation portions.

Having received the rendering condition from the client terminal device 20, the communicating unit 18 transfers the received rendering condition to the synchronization controlling unit 11b. Based on the rendering condition received from the client terminal device 20, the synchronization controlling unit 11b exercises control so that the rendering processing unit 17d performs a volume rendering process.

As a result of the process described above, the operator who made the synchronized display request and the operator of the synchronized display target apparatus are each able to have a stereoscopic view of the volume rendering images obtained by processing the same volume data with the same rendering condition, in compliance with the stereoscopic specifications of the display unit being used by the operator.

Figure 12:
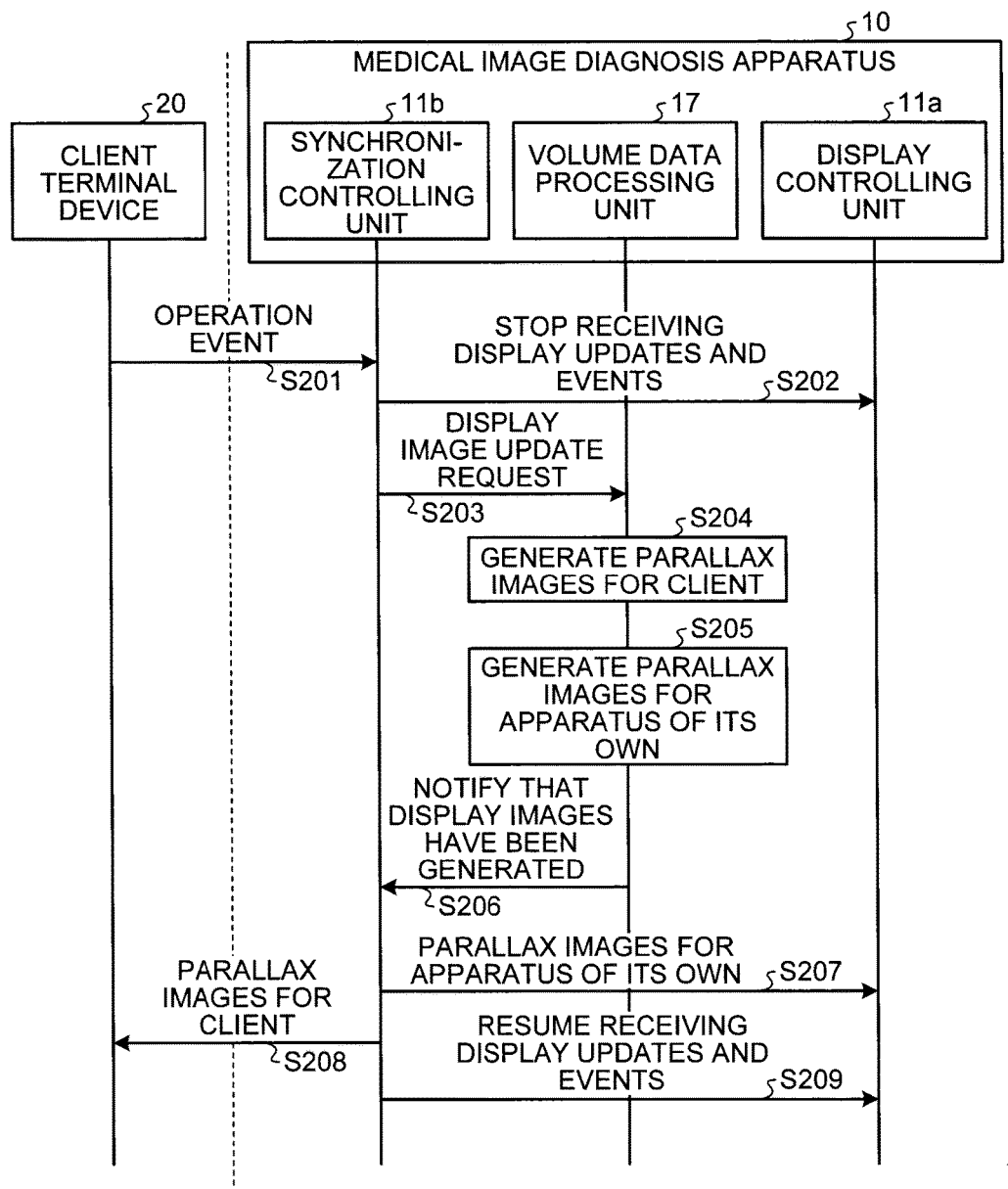
FIG. 12 is a first sequence chart for explaining a synchronized display process performed by a medical image diagnosis apparatus according to the second embodiment.
Figure 13:
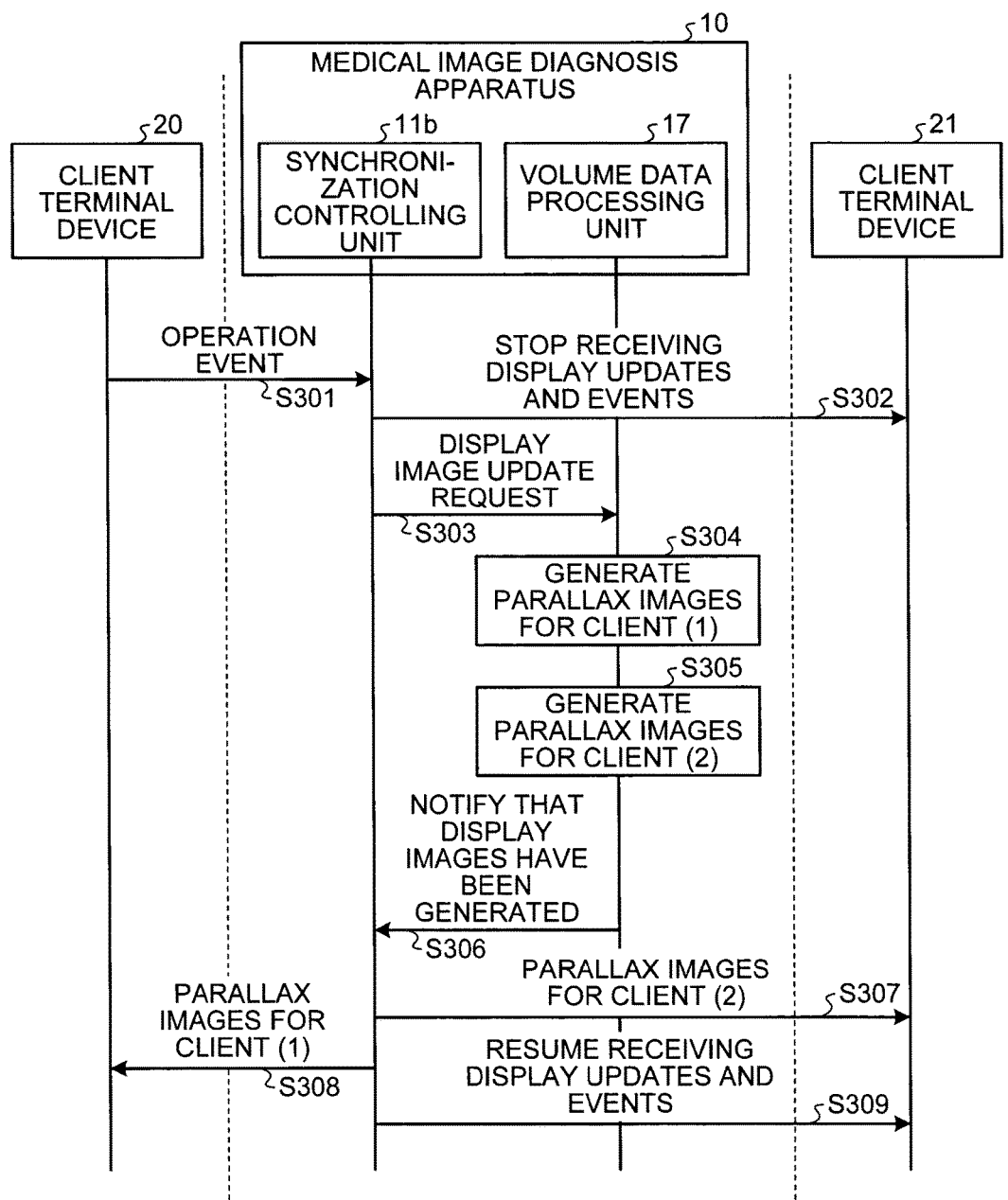
FIG. 13 is a second sequence chart for explaining the synchronized display process performed by the medical image diagnosis apparatus according to the second embodiment.

An example of such a synchronized display process will be explained, with reference to FIGS. 12 and 13. FIGS. 12 and 13 are sequence charts for explaining a synchronized display process performed by the medical image diagnosis apparatus according to the second embodiment. FIG. 12 is a sequence chart of an example in which the operator of the client terminal device 20 takes an initiative and views, in synchronization, the same volume data which is used by the medical image diagnosis apparatus 10 as a rendering target, at the same time as the operator of the medical image diagnosis apparatus 10.

First, as shown in FIG. 12, the client terminal device 20 transmits an operation event indicating a synchronized display request from the operator, to the synchronization controlling unit 11b included in the medical image diagnosis apparatus 10 (step S201). In the example shown in FIG. 12, the client terminal device 20 transmits the operation event indicating that the synchronized display target apparatus is the medical image diagnosis apparatus 10, to the synchronization controlling unit 11b.

Having received the operation event, the synchronization controlling unit 11b notifies the display controlling unit 11a of a request to stop receiving display updates and events intended for the medical image diagnosis apparatus 10 (step S202). The display updates and the events of which the receptions are stopped refer to updates of the images displayed by the display unit 13 and operation events that use the GUI displayed by the display unit 13.

After that, the synchronization controlling unit 11b notifies the volume data processing unit 17 including the rendering processing unit 17d and the stereoscopic image transferring unit 17e of a display image update request corresponding to the received operation event indicating the synchronized display request (step S203). In this situation, the display image update request corresponding to the operation event is a request for generating volume rendering images based on the stereoscopic attributes of the apparatuses having the synchronized display and the rendering condition input by the operator of the client terminal device 20.

Subsequently, the volume data processing unit 17 generates parallax images for the client, as transferred images based on nine-eye parallax images for the client terminal device 20 (step S204). Further, the volume data processing unit 17 generates parallax images for the apparatus of its own that are nine-eye parallax images for the medical image diagnosis apparatus 10 (step S205).

Further, the volume data processing unit 17 notifies the synchronization controlling unit 11b that the display images have been generated (step S206), and the synchronization controlling unit 11b transfers the parallax images for the apparatus of its own to the display controlling unit 11a (step S207). Under the control of the display controlling unit 11a, the display unit 13 displays the parallax images for the apparatus of its own. Subsequently, the synchronization controlling unit 11b transfers the parallax images for the client to the client terminal device 20, via the output unit 18c (step S208).

After that, the synchronization controlling unit 11b notifies the display controlling unit 11a that receptions of display updates and events should be resumed (step S209). If an operation event to change the rendering condition and/or the stereoscopic attributes is transmitted again at step S201, the medical image diagnosis apparatus 10 performs the processes at steps S202 through S208 again.

FIG. 13 is sequence chart of an example in which the operator of the client terminal device 20 takes an initiative and views, in synchronization, the same volume data which is used by the medical image diagnosis apparatus 10 as a rendering target, at the same time as the operator of the client terminal device 21.

First, as shown in FIG. 13, the client terminal device 20 transmits an operation event indicating a synchronized display request from the operator, to the synchronization controlling unit 11b included in the medical image diagnosis apparatus 10 (step S301). In the example shown in FIG. 13, the client terminal device 20 transmits the operation event indicating that the synchronized display target apparatus is the client terminal device 21, to the synchronization controlling unit 11b.

Having received the operation event, the synchronization controlling unit 11b notifies the client terminal device 21 of a request to stop receiving display updates and events (step S302). The display updates and the events of which the receptions are stopped refer to updates of the images displayed by the monitor of the client terminal device 21 and operation events that use the GUI displayed by the monitor of the client terminal device 21.

After that, the synchronization controlling unit 11b notifies the volume data processing unit 17 including the rendering processing unit 17d and the stereoscopic image transferring unit 17e of a display image update request corresponding to the received operation event indicating the synchronized display request (step S303).

Subsequently, the volume data processing unit 17 generates parallax images for client (1), as transferred images based on nine-eye parallax images for the client terminal device 20 (step S304). Further, the volume data processing unit 17 generates parallax images for client (2), as transferred images based on two-eye parallax images for the client terminal device 21 (step S305).

Further, the volume data processing unit 17 notifies the synchronization controlling unit 11b that the display images have been generated (step S306), and the synchronization controlling unit 11b transfers the parallax images for client (2) to the client terminal device 21, via the output unit 18c (step S307). Also, the synchronization controlling unit 11b transfers the parallax images for client (1) to the client terminal device 20, via the output unit 18c (step S308).

After that, the synchronization controlling unit 11b notifies the client terminal device 21 that receptions of display updates and events should be resumed (step S309). If an operation event to change the rendering condition and/or the stereoscopic attributes is transmitted again at step S301, the medical image diagnosis apparatus 10 performs the processes at steps S302 through S308 again.

As explained above, according to the second embodiment, it is possible to display the stereoscopic images in synchronization among the mutually different apparatuses, in compliance with the stereoscopic attributes of the stereoscopic monitor of each of the apparatuses. Thus, even if the viewer is different for each of the apparatuses, the plurality of viewers are able to share the stereoscopic effect. For example, according to the second embodiment, even if nine-eye parallax monitors have not yet been introduced to conference rooms where a plurality of people look at the same screen at a medical office or a radiogram interpretation room that are positioned away from the medical image diagnosis apparatus 10, it is possible to utilize the stereoscopy technology in each of the rooms. Thus, it is possible to easily improve the efficiency in surgery planning and to easily share anatomical information of the patients. In the description above, the examples are explained in which the operator who made the synchronized display request and the operator of the synchronized display target apparatus each have a stereoscopic view of the stereoscopic images that were generated from the same volume data under the same rendering condition and that match the stereoscopic specifications of the display unit used by the operator. However, the second embodiment is also applicable to a situation where, from the same volume data, stereoscopic images that are compliant with the stereoscopic specifications of the display unit used by each of the operators and are compliant with a rendering condition demanded by each of the operators are generated. In other words, the second embodiment is also applicable to the situation where, during the synchronized display process, both of the two operators each change the rendering condition.

Third Embodiment

As a third embodiment, an example will be explained in which, while volume rendering images for realizing a stereoscopic view are stored in the medical image diagnosis apparatus 10, stereoscopic images that are compliant with a request from an apparatus serving as a display-purpose output target are output.

More specifically, the medical image diagnosis apparatus 10 according to the third embodiment stores therein the volume rendering images generated by the rendering processing unit 17d. Further, if no such rendering images that match the stereoscopic attributes and the rendering condition for the volume data received from the display-purpose output target apparatus are stored, the rendering processing unit 17d performs a re-rendering process on the volume data, based on the received information. Further, the output unit 18c outputs the rendering images generated in the re-rendering process performed by the rendering processing unit 17d, to the display-purpose output target apparatus. On the contrary, if such rendering images that match the information related to the stereoscopic functions and the rendering condition for the volume data received from the display-purpose output target apparatus are stored, the medical image diagnosis apparatus 10 according to the third embodiment selects such rendering images and outputs the selected rendering images to the display-purpose output target apparatus.

Figure 14:
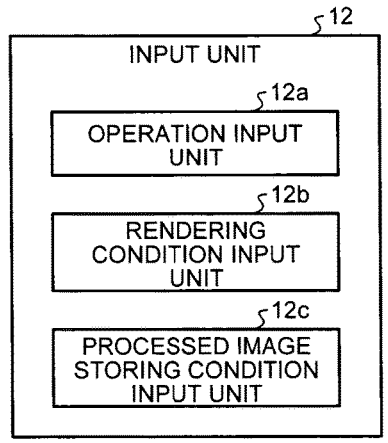
FIG. 14 is a drawing for explaining an exemplary configuration of an input unit according to a third embodiment.

To perform the processes described above, the input unit 12 according to the third embodiment is configured as shown in FIG. 14. FIG. 14 is a drawing for explaining an exemplary configuration of the input unit according to the third embodiment.

As shown in FIG. 14, the input unit 12 according to the third embodiment further includes a processed image storing condition input unit 12c, being different from the input unit 12 shown in FIG. 2. The processed image storing condition input unit 12c receives, from the operator of the medical image diagnosis apparatus 10, a storing condition used for storing the volume rendering images generated by the rendering processing unit 17d. The storing condition received by the processed image storing condition input unit 12c will be explained in detail later.

Figure 15:
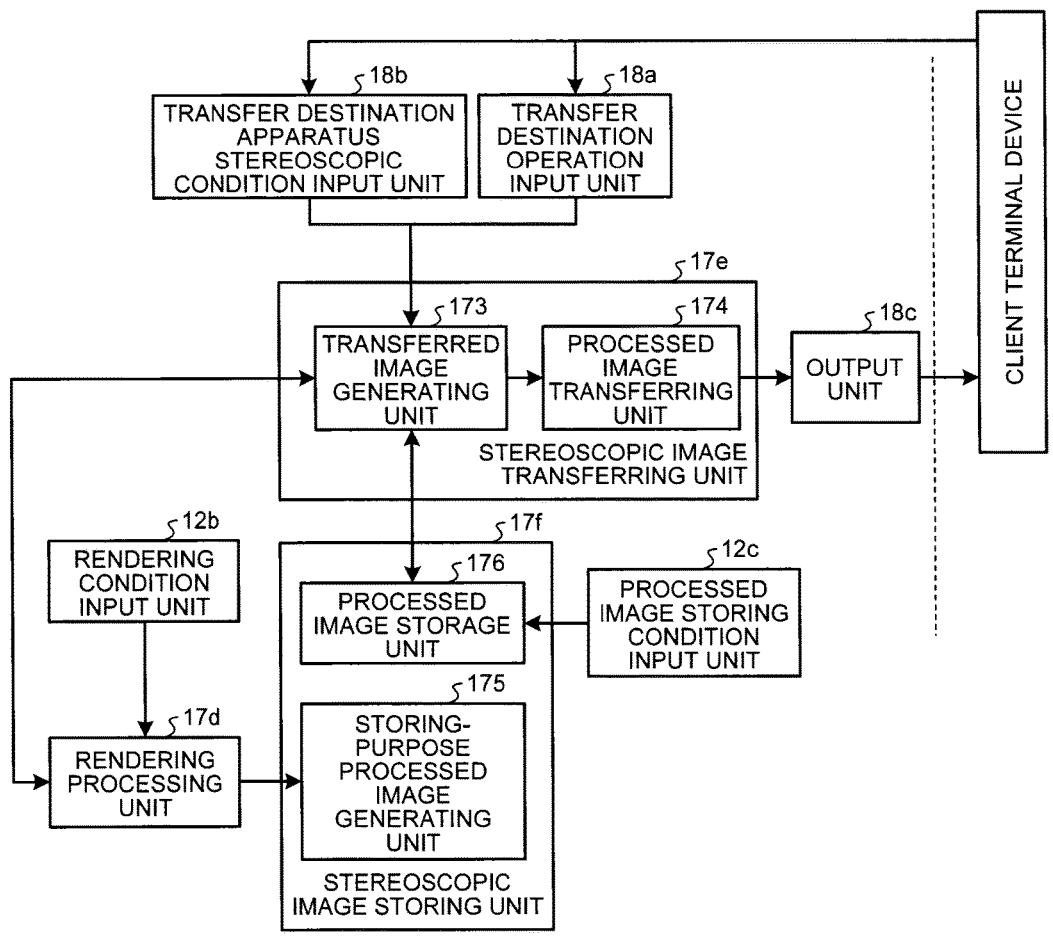
FIG. 15 is a block diagram for explaining processes performed by a rendering processing unit, a stereoscopic image storing unit, a stereoscopic image transferring unit, and an output unit according to the third embodiment.

Further, to perform the processes described above, as shown in FIG. 15, a stereoscopic image storing unit 17f is additionally provided in the third embodiment, which is configured so as to store therein the volume rendering images on which the volume rendering process has been performed, based on the storing condition received by the processed image storing condition input unit 12c. FIG. 15 is a block diagram for explaining processes performed by the rendering processing unit, the stereoscopic image storing unit, the stereoscopic image transferring unit, and the output unit according to the third embodiment. Although not shown in FIG. 15, the processes performed by the functional units are performed under the control of the controlling unit 11.

The rendering processing unit 17d shown in FIG. 15 performs a volume rendering process on the volume data, based on the rendering condition received by the rendering condition input unit 12b. More specifically, the rendering processing unit 17d generates stereoscopic images, based on various conditions such as the stereoscopic attributes of the display unit 13, the viewpoint positions, and the projection method that are received by the rendering condition input unit 12b. The stereoscopic images generated by the rendering processing unit 17d are not limited to the images for the display unit 13 (e.g., nine-eye parallax images). In other words, the rendering processing unit 17d may generate images in a comprehensive manner so as to match any stereoscopic specifications that are currently available including, for example, two-eye parallax images and still images for "non-parallax monitors".

The rendering processing unit 17d shown in FIG. 15 may be configured so as to, when the rendering condition input unit 12b has received a rendering condition change, perform a rendering process again based on the changed rendering condition.

After that, the stereoscopic image storing unit 17f shown in FIG. 15 performs a process to store therein the volume rendering images generated by the rendering processing unit 17d. As shown in FIG. 15, the stereoscopic image storing unit 17f includes a storing-purpose processed image generating unit 175 and a processed image storage unit 176. The storing-purpose processed image generating unit 175 generates storing-purpose processed images by processing the volume rendering images generated by the rendering processing unit 17d, based on the storing condition received by the processed image storing condition input unit 12c.

Figure 16:
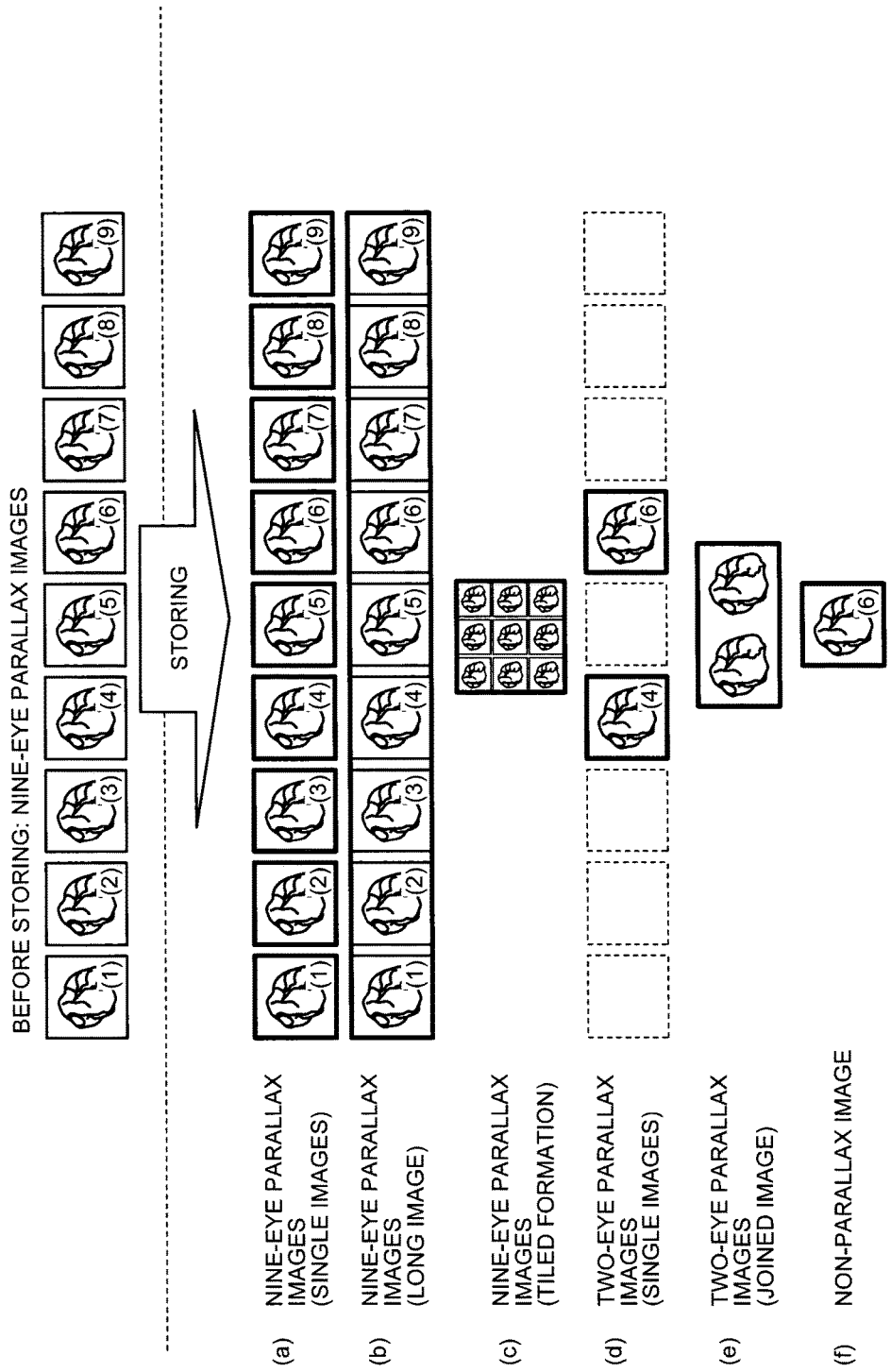
FIG. 16 is a drawing for explaining a storing-purpose processed image generating unit.

FIG. 16 is a drawing for explaining the storing-purpose processed image generating unit. FIG. 16 illustrates an example in which, based on the storing condition received by the processed image storing condition input unit 12c, the storing-purpose processed image generating unit 175 generates storing-purpose processed image from the not-yet-stored nine-eye parallax images generated by the rendering processing unit 17d.

Examples of the storing condition received by the processed image storing condition input unit 12c include: a storing condition indicating that the nine-eye parallax images should be stored as they are so as to be output to a "nine-eye parallax monitor" (a nine-eye parallax storing condition); a storing condition indicating that the nine-eye parallax images should be stored so as to be output to a "two-eye parallax monitor" (a two-eye parallax storing condition); and a storing condition indicating that the nine-eye parallax images should be stored so as to be output to a "non-parallax monitor" (a non-parallax storing condition).

In the following sections, specific examples of the nine-eye parallax storing condition, the two-eye parallax storing condition, and the non-parallax storing condition will be sequentially explained.

An example of the nine-eye parallax storing condition is a condition under which the nine-eye parallax images are individually stored as still images each of which is a single image (see FIG. 16(a)). If a single-image still-image storing condition is received as the nine-eye parallax storing condition, the storing-purpose processed image generating unit 175 generates processed images by using the nine parallax images as nine still images (see the nine bold frames in FIG. 16(a)). Another example of the nine-eye parallax storing condition is a condition under which the nine-eye parallax images are stored as a long image (a moving picture) by being joined altogether (see FIG. 16(b)). If a long-image storing condition is received as the nine-eye parallax storing condition, the storing-purpose processed image generating unit 175 generates a processed image by joining the nine parallax images into one image (see the one bold frame in FIG. 16(b)).

Yet another example of the nine-eye parallax storing condition is a condition under which the nine-eye parallax images are stored, after being converted to intermediate images in a predetermined format (a tiled formation) which can be directly output to a "nine-eye parallax monitor" (see FIG. 16(c)). If an intermediate image conversion condition is received as the nine-eye parallax storing condition, the storing-purpose processed image generating unit 175 generates processed images by arranging the nine parallax images into a tiled formation (see the one bold frame in FIG. 16(c)). In this situation, the intermediate images shown in FIG. 16(c) are generated by arranging the nine parallax images into a grid having three rows and three columns.

An example of the two-eye parallax storing condition is a selecting condition used for selecting two parallax images having a specified parallax angle, from among the nine-eye parallax images. For example, if "parallax angle: 2 degrees" is received as a selecting condition for the two-eye parallax storing condition, the storing-purpose processed image generating unit 175 selects parallax image (4) and parallax image (6). Further, the storing-purpose processed image generating unit 175 determines that parallax image (4) and parallax image (6) will be used as the targets for generating the storing-purpose processed images. Further, by using the storing condition described below that is input together with the selecting condition, the storing-purpose processed image generating unit 175 generates the storing-purpose processed image from parallax image (4) and parallax image (6).

More specifically, an example of the two-eye parallax storing condition is a condition under which the two two-eye parallax images are individually stored as still images each of which is a single image (see FIG. 16(d)). If a single-image still-image storing condition is received as the two-eye parallax storing condition, the storing-purpose processed image generating unit 175 generates processed images by using the two parallax images as two still images (see the two bold frames in FIG. 16(d)). Another example of the two-eye parallax storing condition is a condition under which the two-eye parallax images are stored as a joined image by being joined together (see FIG. 16(e)). If a joined-image storing condition is received as the two-eye parallax storing condition, the storing-purpose processed image generating unit 175 generates a processed image by joining parallax image (4) and parallax image (6) into one still image (see the one bold frame in FIG. 16(e)). As the two-eye parallax storing condition, it is also acceptable to specify a condition under which such images are stored that are able to provide a stereoscopic view even on a non-parallax monitor, by using a parallel view method, a cross-eyed view method, an anaglyphic method, or the like.

An example of the non-parallax storing condition is a selecting condition used for selecting a parallax image corresponding to one specified viewpoint position, from among the nine nine-eye parallax images. For example, based on a selecting condition for the non-parallax storing condition, the storing-purpose processed image generating unit 175 selects parallax image (6). Further, the storing-purpose processed image generating unit 175 generates a storing-purpose processed image by using parallax image (6) as a target. Under the non-parallax storing condition, because the target image is one, the storing-purpose processed image generating unit 175 generates a processed image by using parallax image (6) as a still image (see the one bold frame in FIG. 16(f)). If a moving picture display selecting condition is received as a selecting condition for the non-parallax storing condition, the storing-purpose processed image generating unit 175 performs the process of storing the nine-eye parallax images as the long image as described above. As another example, if a side-by-side display selecting condition is received as a selecting condition for the non-parallax storing condition, the storing-purpose processed image generating unit 175 performs the process of storing the nine-eye parallax images as the single-image still-image as described above. As the non-parallax storing condition, it is also acceptable to specify a condition under which such images are stored that are able to provide a stereoscopic view even on a non-parallax monitor, by using a parallel view method, a cross-eyed view method, an anaglyphic method, or the like.

After that, the storing-purpose processed image generating unit 175 stores the one or more generated processed images into the processed image storage unit 176 shown in FIG. 15. In this situation, the processed image storage unit 176 is configured with a HDD, like the image storage unit 16. The storing condition received by the processed image storing condition input unit 12c may be all of the nine-eye parallax storing condition, the two-eye parallax storing condition, and the non-parallax storing condition or may be two selected out of the nine-eye parallax storing condition, the two-eye parallax storing condition, and the non-parallax storing condition.

An arrangement is acceptable in which the storing-purpose processed image generating unit 175 stores, into the processed image storage unit 176, accompaniment information such as the parallax number, the parallax angle, a monitor name used as a target during the storing process, in correspondence with the processed images. Further, the monitor name included in the accompaniment information may be one monitor name or may be a plurality of monitor names having mutually the same stereoscopic attributes.

Returning to the description of FIG. 15, the stereoscopic image transferring unit 17e includes, like in the first embodiment, the transferred image generating unit 173 configured to generate the transferred images to be transferred to the apparatus serving as a display-purpose output target (a client terminal device in the example shown in the drawing) and the processed image transferring unit 174 configured to output the transferred images to the output unit 18c. Like in the first embodiment, the transfer destination apparatus stereoscopic condition input unit 18b shown in FIG. 15 receives the stereoscopic attributes of the monitor of the apparatus serving as a display-purpose output target. Also, like in the first embodiment, the transfer destination operation input unit 18a shown in FIG. 15 receives a rendering condition for the volume data.

In this situation, the transferred image generating unit 173 according to the third embodiment judges whether such volume rendering images (processed images) that match the stereoscopic attributes of the monitor of the apparatus serving as a display-purpose output target and the rendering condition input by the operator of the apparatus serving as the display-purpose output target are stored in the processed image storage unit 176. If such volume rendering images are stored, the transferred image generating unit 173 obtains such volume rendering images (processed images) from the processed image storage unit 176 and generates transferred images. Like in the first embodiment, the transferred images are transferred to the apparatus serving as a display-purpose output target, as a result of the processes performed by the processed image transferring unit 174 and the output unit 18c. The transferred image generating unit 173 according to the third embodiment may be configured, like in the first embodiment, so as to generate the transferred images after selecting such processed images that match the stereoscopic attributes and the rendering condition from among the already-stored processed images. For example, the transferred image generating unit 173 may generate the transferred images by selecting two-eye parallax images from among already-stored nine-eye parallax images or may generate the transferred images by selecting three-eye parallax images from among already-stored five-eye parallax images.

On the contrary, if no such volume rendering images (processed images) that match the stereoscopic attributes and the rendering condition are stored in the processed image storage unit 176, the transferred image generating unit 173 according to the third embodiment requests the rendering processing unit 17d to perform a re-rendering process.

More specifically, like in the first embodiment, the rendering processing unit 17d performs a volume rendering process on the volume data again, based on various types conditions such as the parallax number, the viewpoint positions, the display attributes (the appearance attributes), and the projection method. The volume rendering images for realizing a stereoscopic view that were generated again by the rendering processing unit 17d are arranged to be transferred images by the stereoscopic image transferring unit 17e and are output from the output unit 18c. The volume rendering images for realizing a stereoscopic view that were generated again by the rendering processing unit 17d may be transferred to the stereoscopic image storing unit 17f to be stored as processed images and may subsequently be arranged to be transferred images by the stereoscopic image transferring unit 17e, before being output from the output unit 18c. If the operator of the output destination apparatus who has viewed the transferred images output from the output unit 18c changes the rendering condition, the rendering processing unit 17d performs, like in the first embodiment, a volume rendering process again based on the changed rendering condition.

The output unit 18c may attach exclusive-use software (a dedicated viewing tool) used for viewing the transferred images, to the transferred images. It should be noted, however, that the apparatus at the transfer destination exercises control according to the parallax number of the display device thereof, when causing the dedicated viewing tool to expand and display the transferred images to realize a stereoscopic view.

Figure 17:
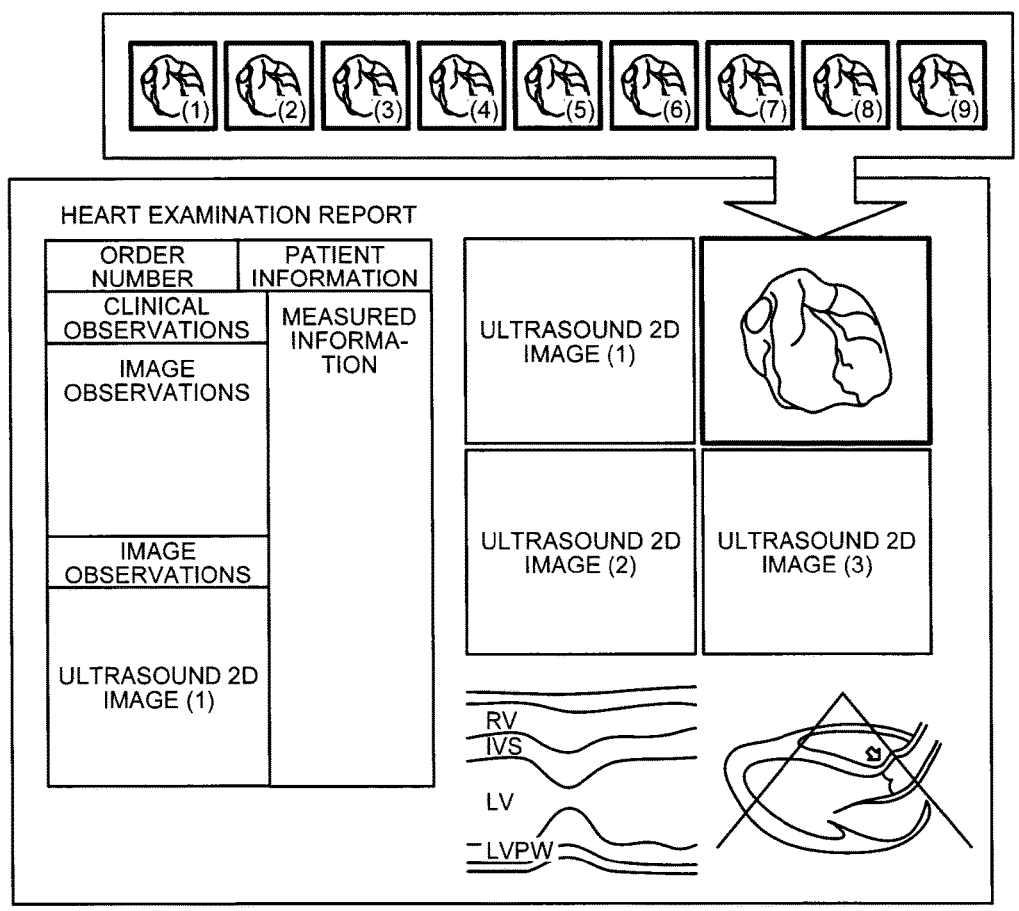
FIG. 17 is a drawing for explaining an example with images output by a medical image diagnosis apparatus according to the third embodiment.

In this situation, the images for realizing a stereoscopic view that have been stored may be stored as being attached to a report or a document and may be transferred for a display purpose in response to a request from, for example, the client terminal device 20. FIG. 17 is a drawing for explaining an example with images output by a medical image diagnosis apparatus according to the third embodiment. The example shown in FIG. 17 illustrate a situation in which the nine-eye parallax images that match a request from the client terminal device 20 are stored as being attached to a heart examination report within the processed image storage unit 176.

More specifically, in the example shown in FIG. 17, laid out in a report called "heart examination report" are text information such as a heart examination report, an examination order number, patient information, image observations, and measured information, as well as two-dimensional image data such as ultrasound 2D image (1), ultrasound 2D image (2), ultrasound 2D image (3), and also, data roughly rendering the image taking site in which an ultrasound scan was performed. As a part of the layout of the "heart examination report", a viewing tool is pasted. As shown in FIG. 17, the viewing tool is provided with nine-eye parallax images, as display-purpose contents.

When such a report is output to the client terminal device 20, the viewing tool is activated. In compliance with the specifications of the monitor (the nine-eye parallax monitor) of the client terminal device 20, the viewing tool converts the nine-eye parallax images, which are the display-purpose contents, into intermediate images and outputs the intermediate images. As a result, the operator of the client terminal device 20 is able to have a stereoscopic view of some of the images in the heart examination report that are of importance, by using a binocular parallax and a motion parallax.

The layout process for the stereoscopic images within the report may be performed by the client terminal device 20 having received the nine-eye parallax images.

Figure 18:
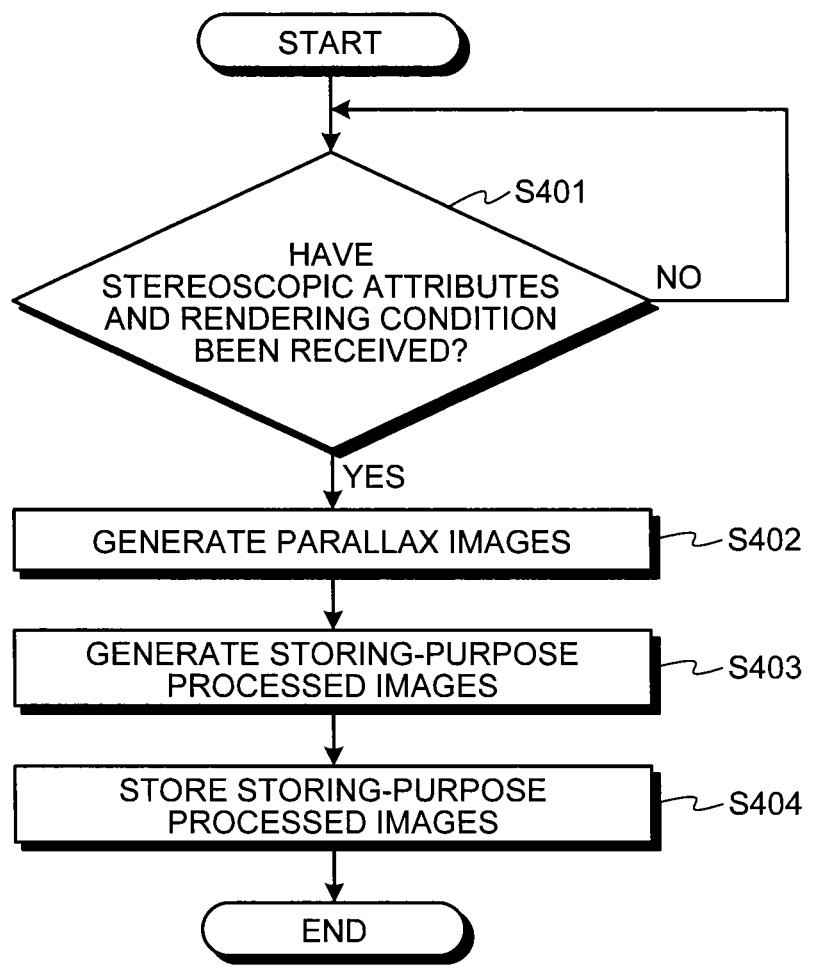
FIG. 18 is a flowchart for explaining an image storing process performed by the medical image diagnosis apparatus according to the third embodiment.
Figure 19:
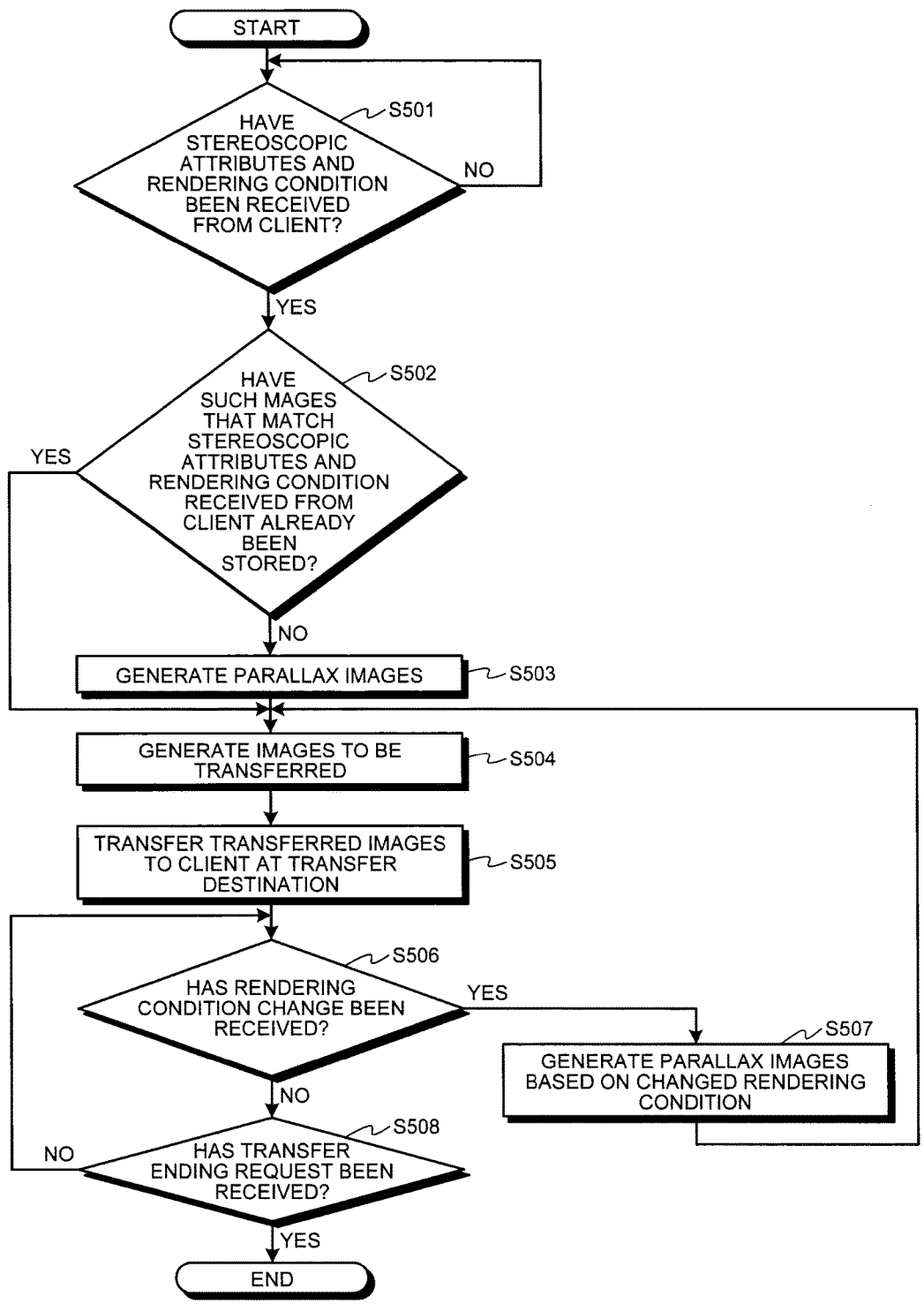
FIG. 19 is a flowchart for explaining an output process performed by the medical image diagnosis apparatus according to the third embodiment.

Next, processes performed by the medical image diagnosis apparatus according to the third embodiment will be explained, with reference to FIGS. 18 and 19. FIG. 18 is a flowchart for explaining an image storing process performed by the medical image diagnosis apparatus according to the third embodiment. FIG. 19 is a flowchart for explaining an output process performed by the medical image diagnosis apparatus according to the third embodiment.

As shown in FIG. 18, the medical image diagnosis apparatus 10 according to the third embodiment judges whether the rendering condition input unit 12b has received stereoscopic attributes and a rendering condition (step S401). In this situation, if stereoscopic attributes and a rendering condition have not been received (step S401: No), the medical image diagnosis apparatus 10 according to the third embodiment goes into a standby state.

On the contrary, if stereoscopic attributes and a rendering condition have been received (step S401: Yes), the rendering processing unit 17d generates parallax images (volume rendering images) based on the received stereoscopic attributes and rendering condition (step S402).

Based on the storing condition received by the processed image storing condition input unit 12c, the storing-purpose processed image generating unit 175 generates storing-purpose processed images (step S403). Further, the storing-purpose processed image generating unit 175 stores the storing-purpose processed images into the processed image storage unit 176 (step S404) and ends the process.

After that, as shown in FIG. 19, the medical image diagnosis apparatus 10 according to the third embodiment judges whether stereoscopic attributes and a rendering condition have been received from a client that is a display-purpose output target apparatus, via the transfer destination apparatus stereoscopic condition input unit 18b and the transfer destination operation input unit 18a (step S501). In this situation, if stereoscopic attributes and a rendering condition have not been received from the client (step S501: No), the medical image diagnosis apparatus 10 according to the third embodiment goes into a standby state.

On the contrary, if stereoscopic attributes and a rendering condition have been received from the client (step S501: Yes), the transferred image generating unit 173 judges whether such images that match the stereoscopic attributes and the rendering condition received from the client have already been stored (step S502). If no such images have been stored (step S502: No), the rendering processing unit 17d generates parallax images that match the stereoscopic attributes and the rendering condition received from the client, in response to a request from the transferred image generating unit 173 (step S503). After that the stereoscopic image transferring unit 17e generates transferred images (step S504).

On the contrary, if such images have been stored (step S502: Yes), the transferred image generating unit 173 obtains the matching parallax images from the processed image storage unit 176 and generates transferred images (step S504).

The output unit 18c transfers the transferred images to the client at the transfer destination (step S505), and the transfer destination operation input unit 18a judges whether a rendering condition change has been received (step S506). If a rendering condition change has been received (step S506: Yes), the rendering processing unit 17d generates parallax images based on the changed rendering condition (step S507). After that, the medical image diagnosis apparatus 10 performs the processes at step S504 and thereafter.

On the contrary, if no rendering condition change is received (step S506: No), the controlling unit 11 judges whether a transfer ending request has been received (step S508). In this situation, if no transfer ending request is received (step S508: No), the process returns to step S506, where it is judged whether a rendering condition change has been received.

On the contrary, if a transfer ending request has been received (step S508: Yes), the medical image diagnosis apparatus 10 according to the third embodiment ends the process.

As explained above, according to the third embodiment, even if the stereoscopic images are temporarily stored into the medical image diagnosis apparatus 10, another apparatus is also able to, by making a remote access to the medical image diagnosis apparatus 10, display the stored stereoscopic images in such a manner as to be able to provide a stereoscopic view on the accessing apparatus. As a result, even if the medical image diagnosis apparatus 10 is to be installed with a nine-eye parallax monitor, it is possible to continuously use an already-structured intra-hospital network.

Fourth Embodiment

As a fourth embodiment, an example will be explained in which, while the volume rendering images for realizing a stereoscopic view are stored in the medical image diagnosis apparatus 10, stereoscopic images and the like that are compliant with a request from an apparatus serving as a storing-purpose output target are output for a storing purpose.

More specifically, like in the third embodiment, the medical image diagnosis apparatus 10 according to the fourth embodiment stores therein the volume rendering images generated by the rendering processing unit 17d. Further, if no such rendering images that match the stereoscopic attributes and the rendering condition for the volume data received from the apparatus serving as a storing-purpose output target are stored, the rendering processing unit 17d performs a re-rendering process on the volume data based on the rendering condition. After that, the output unit 18c outputs the rendering images generated in the re-rendering process performed by the rendering processing unit 17d, to the storing-purpose output target apparatus.

To perform the processes described above, the communicating unit 18 according to the fourth embodiment is configured as shown in FIG. 20. FIG. 20 is a drawing for explaining an exemplary configuration of the communicating unit according to the fourth embodiment.

Being different from the communicating unit 18 shown in FIG. 2, the communicating unit 18 according to the fourth embodiment includes, as shown in FIG. 20, a storing-purpose condition input unit 18d and a storing-purpose output destination stereoscopic condition input unit 18e, in place of the transfer destination operation input unit 18a and the transfer destination apparatus stereoscopic condition input unit 18b. The storing-purpose condition input unit 18d is an input unit corresponding to the transfer destination operation input unit 18a and is configured to receive a rendering condition from the apparatus serving as a storing-purpose output target. Further, the storing-purpose output destination stereoscopic condition input unit 18e is an input unit corresponding to the transfer destination apparatus stereoscopic condition input unit 18b and is configured to receive stereoscopic attributes from the apparatus serving as a storing-purpose output target.

Like in the third embodiment, the medical image diagnosis apparatus 10 according to the fourth embodiment includes the stereoscopic image storing unit 17f, as shown in FIG. 21. Further, the medical image diagnosis apparatus 10 according to the fourth embodiment includes a storing-purpose output processing unit 17g, in place of the stereoscopic image transferring unit 17e, as shown in FIG. 21. Further, the medical image diagnosis apparatus 10 according to the fourth embodiment is configured so that the storing-purpose output process described above is performed by the rendering processing unit 17d, the stereoscopic image storing unit 17f, the storing-purpose output processing unit 17g, and the output unit 18c, working in collaboration with one another.

FIG. 21 is a block diagram for explaining processes performed by the rendering processing unit, the stereoscopic image storing unit, the storing-purpose output processing unit, and the output unit according to the fourth embodiment. FIG. 21 illustrates an example in which the apparatus serving as a storing-purpose output target is the image storing apparatus 31. Alternatively, the apparatus serving as a storing-purpose output target may be the portable storage apparatus 40 shown in FIG. 1. Also, although not shown in FIG. 21, the processes performed by the functional units are performed under the control of the controlling unit 11.

Like in the third embodiment, the rendering processing unit 17d shown in FIG. 21 performs the volume rendering process on the volume data, based on the rendering condition received by the rendering condition input unit 12b.

After that, like in the third embodiment, the stereoscopic image storing unit 17f shown in FIG. 21 performs a process of storing the volume rendering images generated by the rendering processing unit 17d, based on the storing condition received by the processed image storing condition input unit 12c.

Further, the storing-purpose output processing unit 17g shown in FIG. 21 includes a storing-purpose output image generating unit 177 corresponding to the transferred image generating unit 173 and a storing-purpose output image output unit 178 corresponding to the processed image transferring unit 174.

More specifically, the storing-purpose output image generating unit 177 judges whether such volume rendering images (processed images) that match the stereoscopic attributes requested by the apparatus serving as a storing-purpose output target and the rendering condition input by the operator of the apparatus serving as the storing-purpose output target are stored in the processed image storage unit 176. If such volume rendering images are stored, the storing-purpose output image generating unit 177 obtains such volume rendering images (processed images) from the processed image storage unit 176 and generates storing-purpose output images by performing an image compression process. Like the transferred images explained in the first to the third embodiments, the storing-purpose output images are transferred to the apparatus serving as a storing-purpose output target, as a result of the processes performed by the storing-purpose output image output unit 178 and the output unit 18c. Like the transferred image generating unit 173 according to the third embodiment, the storing-purpose output image generating unit 177 may be configured so as to generate the storing-purpose output images after selecting such processed images that match the stereoscopic attributes and the rendering condition from among the already-stored processed images.

On the contrary, if no such volume rendering images (processed images) that match the stereoscopic attributes and the rendering condition are stored in the processed image storage unit 176, the storing-purpose output image generating unit 177 requests the rendering processing unit 17d to perform a re-rendering process, like the transferred image generating unit 173 according to the third embodiment.

Further, if the operator of the storing-purpose output destination apparatus who has viewed the storing-purpose output images output from the output unit 18c changes a rendering condition, the rendering processing unit 17d performs a volume rendering process again, based on the changed rendering condition, like in the first to the third embodiments.

The image storing process performed by the medical image diagnosis apparatus 10 according to the fourth embodiment is the same as the image storing process performed by the medical image diagnosis apparatus 10 according to the third embodiment explained with reference to FIG. 18. Thus, the explanation thereof will be omitted. Further, the storing-purpose output process performed by the medical image diagnosis apparatus 10 according to the fourth embodiment is almost the same as the display-purpose output process performed by the medical image diagnosis apparatus 10 according to the third embodiment explained with reference to FIG. 19, except that the storing-purpose condition input unit 18d and the storing-purpose output destination stereoscopic condition input unit 18e receive the various types of information, in place of the transfer destination operation input unit 18a and the transfer destination apparatus stereoscopic condition input unit 18b. Thus, the explanation thereof will be omitted.

As explained above, according to the fourth embodiment, even if the stereoscopic images are temporarily stored into the medical image diagnosis apparatus 10 like in the third embodiment, another apparatus is also able to, by making a remote access to the medical image diagnosis apparatus 10, store therein the stored stereoscopic images in such a manner as to be able to provide a stereoscopic view on the accessing apparatus. It is also acceptable to configure the fourth embodiment so that, after the stereoscopic images that are in compliant with a request from the apparatus serving as a storing-purpose output target are generated, the generated stereoscopic images are output to the apparatus for a storing purpose.

Figure 22:
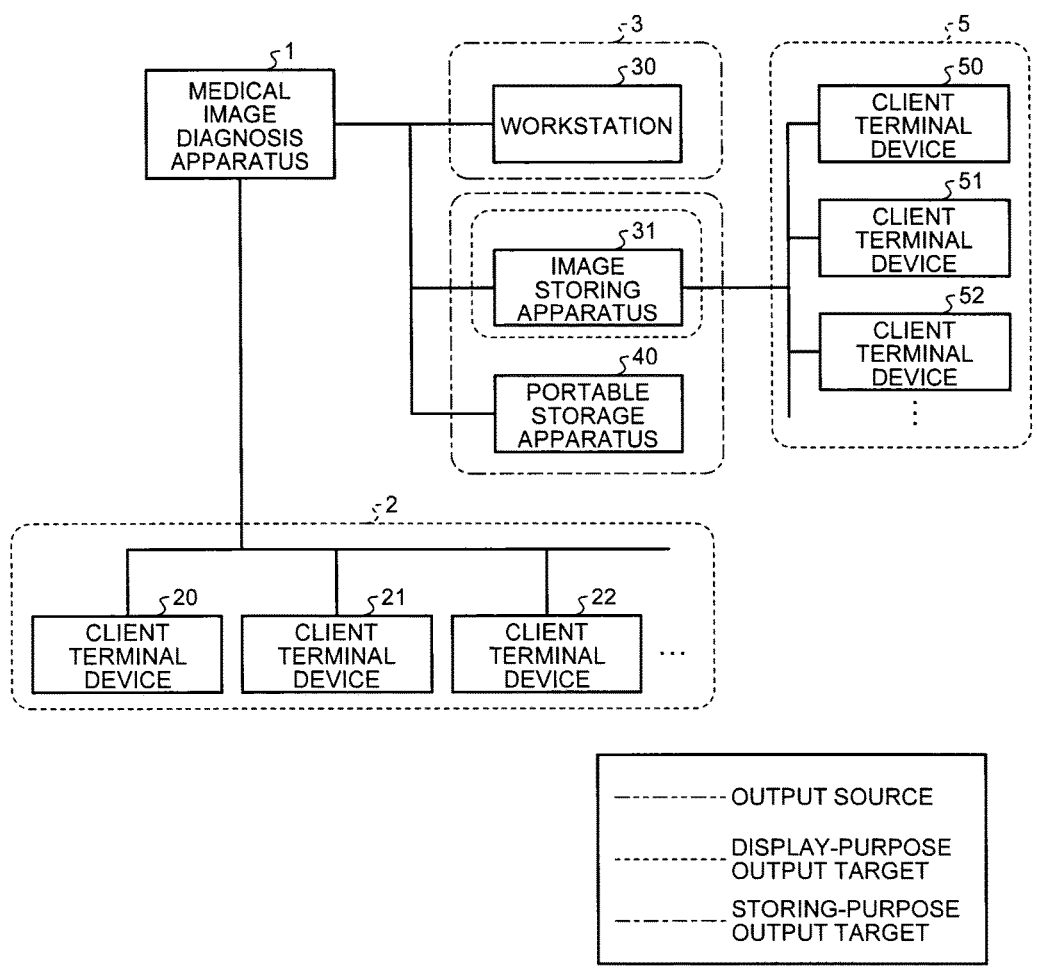
FIG. 22 is a drawing for explaining a modification example of configurations of medical image processing systems according to the first to the fourth embodiments.

In the first to the fourth embodiments described above, the examples are explained in which the medical image diagnosis apparatus 10 performs the rendering process on the volume data. However, the first to the fourth embodiments are also applicable to a situation in which the workstation 30 that has image processing functions performs a rendering process on the volume data. FIG. 22 is a drawing for explaining a modification example of the configurations of the medical image processing systems according to the first to the fourth embodiments.

For example, according to the present modification example, as shown in FIG. 22, a group of medical image diagnosis apparatuses 1 including various types of medical image diagnosis apparatuses 10 is connected to an intra-hospital LAN. The group of medical image diagnosis apparatuses 1 generates volume data such as three-dimensional X-ray images, three-dimensional X-ray CT images, three-dimensional MRI images, and the like. Further, the workstation 30 shown in FIG. 22 performs a rendering process on the volume data directly received from the group of medical image diagnosis apparatuses 1 or on the volume data received from the group of medical image diagnosis apparatuses 1 via the image storing apparatus 31. In other words, the workstation 30 shown in FIG. 22 has the functions of the rendering processing unit 17d, the input unit 12, and the communicating unit 18 explained in the first to the fourth embodiments.

In this configuration, the workstation 30 serves as an output source of the rendering images, as shown in FIG. 22. Also, as shown in FIG. 22, the workstation 30 uses the group of medical image diagnosis apparatuses 1, the group of client terminal devices 2, the image storing apparatus 31, and the group of client terminal devices 5, as display-purpose output targets of the rendering images. Also, as shown in FIG. 22, the workstation 30 uses the image storing apparatus 31 and the portable storage apparatus 40 as storing-purpose output targets of the rendering images.

In other words, the medical image processing systems according to the first to the fourth embodiments may be realized by providing the workstation 30 in place of the medical image diagnosis apparatus 10, as a medical image processing apparatus configured to perform the image processing process for realizing the stereoscopic view on the volume data. Alternatively, the medical image processing systems according to the first to the fourth embodiments are applicable to a situation where the medical image processing apparatus configured to perform the image processing process for realizing the stereoscopic view on the volume data is the group of client terminal devices 2. Further, the functions of the medical image diagnosis apparatus 10 that serves as a medical image processing apparatus explained in the first to the fourth embodiments may be realized as being distributed to any of the apparatuses illustrated in FIG. 1 or FIG. 22.

In the exemplary embodiments described above, the example is explained in which the rendering processing unit 17d determines the parallax number and the parallax angle to be output to the display unit of the output target apparatus, based on the stereoscopic attributes. However, the exemplary embodiments described above may be configured so that a determining process is performed as described below, based on a resolution level of the parallax images and positional arrangement information of the parallax images that are obtained as the stereoscopic attributes of the display unit of the output target apparatus. More specifically, the rendering processing unit 17d changes the resolution level of the rendering images corresponding to the parallax images, based on the resolution level of the parallax images that is obtained as the information related to the stereoscopic functions. For example, if a resolution level "512 pixels by 512 pixels" of the nine-eye parallax images to be displayed on the nine-eye parallax monitor of the client terminal device 20 is obtained as a stereoscopic attribute, the rendering processing unit 17d determines that the rendering images corresponding to the parallax images should be generated with a resolution level of "512 pixels by 512 pixels".

Further, the rendering processing unit 17d changes a positional arrangement of the parallax images that are output from the output unit 18c, based on the positional arrangement information of the parallax images that is obtained as the information related to the stereoscopic functions. In the exemplary embodiments above, the example is explained in which, when being output to the nine-eye parallax monitor, the nine parallax images are converted into the intermediate images arranged in the tiled formation having three rows and three columns. However, the format of the intermediate images into which the nine-eye parallax images are converted when being output to the nine-eye parallax monitor is not limited to the tiled formation having three rows and three columns. For example, the format of the intermediate images may be configured so that the nine parallax images are arranged into a grid having "1 row and 9 columns", "9 rows and 1 column", or "2 rows and 5 columns", depending on the specifications of the nine-eye parallax monitor. In that situation, for example, if the positional arrangement information of the parallax images that is obtained as the information related to the stereoscopic functions indicates "2 rows and 5 columns", the rendering processing unit 17d transmits an instruction to the stereoscopic image transferring unit 17e so that the output unit 18c outputs intermediate images obtained by arranging the nine-eye parallax images into a grid having "2 rows and 5 columns".

The constituent elements of the apparatuses illustrated in the drawings are based on functional concepts. Thus, it is not necessary to physically configure the constituent elements as indicated in the drawings. In other words, the specific modes of distribution and integration of the apparatuses are not limited to the ones shown in the drawings. It is acceptable to functionally or physically distribute or integrate all or a part of the apparatuses in any arbitrary units, depending on various loads and the status of use. For example, the transfer destination operation input unit 18a and the transfer destination apparatus stereoscopic condition input unit 18b may be integrated together. As another example, the process to determine the parallax image number (the parallax number) and the like based on the stereoscopic attributes may be performed by the controlling unit 11, for example, instead of by the rendering processing unit 17d. Further, all or an arbitrary part of the processing functions performed by the apparatuses may be realized by a Central Processing Unit (CPU) and a computer program that is analyzed and executed by the CPU or may be realized as hardware using wired logic.

It is possible to realize any of the medical image processing methods explained in the exemplary embodiments above, by causing a computer such as a personal computer or a workstation to execute a medical image processing computer program prepared in advance. It is possible to distribute the medical image processing computer program via a network such as the Internet. Also, the computer program may be recorded on a computer-readable recording medium such as a hard disk, a flexible disk (FD), a CD-ROM, an MO, a DVD, or the like, so as to be executed as being read by a computer from the recording medium.

As explained above, according to the first to the fourth embodiments, it is possible to enable the viewer to have a stereoscopic view of the three-dimensional medical images in compliance with each stereoscopic method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing system comprising:
   a first display that is connected to a first output target apparatus serving as an output target; and
   a processor that is connected to a memory, wherein
   the memory is configured to store volume data that represents three-dimensional medical images; and
   the processor is configured to:
      obtain first information related to a stereoscopic function of the first display, the first information indicating a first parallax image number and a first parallax angle of images that are for realizing a stereoscopic view and are to be displayed by the first display;
      generate first parallax images based on the first parallax image number and the first parallax angle indicated by the first information, by performing a rendering process on the volume data stored in the memory;
      output the first parallax images to the first output target apparatus; and
      store the first parallax images to the memory;
   the medical image processing system further comprising a second display that is connected to a second output target apparatus serving as the output target;
   the processor is further configured to:
      obtain second information related to a stereoscopic function of the second display, the second information indicating a second parallax image number and a second parallax angle of images that are for realizing a stereoscopic view and are to be displayed by the second display,
      determine whether second parallax images that match the second information exist among the first parallax images stored in the memory,
      if such second parallax images exist, output the second parallax images to the second output target apparatus, and
      if no such second parallax images exist, perform a re-rendering process on the volume data, based on the second information, and output parallax images generated in the re-rendering process to the second output target apparatus.

2. The medical image processing system according to claim 1, wherein at least one of the first display and the second display is an apparatus configured such that a pair of images that is for realizing a stereoscopic view and is visible to a viewer is changed according to a viewing direction.

3. The medical image processing system according to claim 1, wherein the first parallax image number is changed based on a number of viewing directions to which the first display realizes a stereoscopic view corresponding, and the second parallax image number is changed based on a number of viewing directions to which the second display realizes a stereoscopic view corresponding.

4. The medical image processing system according to claim 1, further comprising the input configured to receive the first information and the second information, wherein
the processor is further configured to determine the first parallax image number based on the first information that is received by the input, and determine the second parallax image number based on the second information that is received by the input.

5. The medical image processing system according to claim 4, wherein
the input further receives a change request for changing a rendering condition for the volume data,
the processor is further configured to perform a re-rendering process on the volume data, based on the change request received by the input,
the processor is further configured to output first parallax images generated by the re-rendering process, to the first output target apparatus, and
the processor is further configured to store the first parallax images generated by the re-rendering process to the memory.

6. The medical image processing system according to claim 4, wherein
there are a plurality of output target apparatuses including the first output target apparatus and the first output target apparatus,
the processor is further configured to determine a parallax image number and a parallax angle for each of the plurality of output target apparatuses, based on information that is received by the input and is related to a stereoscopic function of each of displays respectively connected to the plurality of output target apparatuses, the information indicating the parallax image number and the parallax angle for each of the plurality of output target apparatuses,
the processor is further configured to perform a rendering process on the volume data, based on the parallax image number, the parallax angle, and the rendering condition for the volume data received by the input that are for each of the plurality of output target apparatuses, and
the processor is further configured to output parallax images for each of the plurality of output target apparatuses to a corresponding one of the output target apparatuses, in synchronization among the output target apparatuses.

7. The medical image processing system according to claim 1, wherein, to the first output target apparatus having the first display configured to switch among images realizing a stereoscopic view at predetermined time intervals, the processor is further configured to output a group of the first parallax images for the first output target apparatus, while switching among the first parallax images in the group at the predetermined time intervals.

8. The medical image processing system according to claim 1, wherein, based on positional arrangement information of the first parallax images that is obtained as the first information, the processor is further configured to change a positional arrangement of the first parallax images to be output from the processor.

9. The medical image processing system according to claim 1, wherein, based on a resolution level of the first parallax images that is obtained as the fit information related to the stereoscopic function, the processor is further configured to change a resolution level of the first parallax images corresponding to the first parallax images.

10. A medical image processing apparatus comprising:
a first display that is connected to a first output target apparatus serving as an output target; and
a processor that is connected to a memory, wherein
the memory is configured to store volume data that represents three-dimensional medical images and
the processor is configured to:
obtain first information related to a stereoscopic function of the first display, the first information indicating a first parallax image number and a first parallax angle of images that are for realizing a stereoscopic view and are to be displayed by the first display;
generate first parallax images based on the first parallax image number and the first parallax angle indicated by the first information, by performing a rendering process on the volume data stored in the memory;
output the first parallax images to the first output target apparatus; and
store the first parallax images to the memory;
the medical image processing system further comprising a second display that is connected to a second output target apparatus serving as the output target;
the processor is further configured to:
obtain second information related to a stereoscopic function of the second display, the second information indicating a second parallax image number and a second parallax angle of images that are for realizing a stereoscopic view and are to be displayed by the second display,
determine whether second parallax images that match the second information exist among the first parallax images stored in the memory,
if such second parallax images exist, output the second parallax images to the second output target apparatus, and
if no such second parallax images exist, perform a re-rendering process on the volume data, based on the second information, and output parallax images generated in the re-rendering process to the second output target apparatus.

11. A medical image diagnosis apparatus comprising:
a first display that is connected to a first output target apparatus serving as an output target; and
a processor that is connected to a memory, wherein
the memory is configured to store volume data that represents three-dimensional medical images and
the processor is configured to:
generate volume data that represents three-dimensional medical images;
obtain first information related to a stereoscopic function of the display, the first information indicating a first parallax image number and a first parallax angle of images that are for realizing a stereoscopic view and are to be displayed by the first display;
generate first parallax images based on the fist parallax image number and the first parallax angle indicated by the first information, by performing a rendering process on the volume data stored in the memory;

output the first parallax images to the first output target apparatus; and store the first parallax images to the memory;

the medical image processing system further comprising a second display that is connected to a second output target apparatus serving as the output target;

the processor is further configured to:

obtain second information related to a stereoscopic function of the second display, the second information indicating a second parallax image number and a second parallax angle of images that are for realizing a stereoscopic view and are to be displayed by the second display, determine whether second parallax images that match the second information exist among the first parallax images stored in the memory, if such second parallax images exist, output the second parallax images to the second output target apparatus, and if no such second parallax images exist, perform a re-rendering process on the volume data, based on the second information, and output parallax images generated in the re-rendering process to the second output target apparatus.

12. A medical image processing method comprising:

a first obtaining step of, using a processor, obtaining first information related to a stereoscopic function of a first display that is connected to a first output target apparatus serving as an output target, the first information indicating a first parallax image number and a first parallax angle of images that are for realizing a stereoscopic view and are to be displayed by the first display;

a rendering processing step of, using the processor, generating first parallax images based on the first parallax image number and the first parallax angle indicated by the first information, by performing a rendering process on the volume data stored in the memory;

a first outputting step of, using the processor, outputting the first parallax images to the first output target apparatus;

a storing step of, using the processor, storing the first parallax images to the memory;

a second obtaining step of, using the processor, obtaining second information related to a stereoscopic function of the second display that is connected to a second output target apparatus serving as the output target the second information indicating a second parallax image number and a second parallax angle of images that are for realizing a stereoscopic view and are to be displayed by the second display;

a determining step of, using the processor, determining whether second parallax images that match the second information exist among the first parallax images stored in the memory;

a second outputting step of, using the processor, if such second parallax images exist, outputting the second parallax images to the second output target apparatus; and a third outputting step of, using the processor, if no such second parallax images exist, performing a re-rendering process on the volume data, based on the second information, and outputting parallax images generated in the re-rendering process to the second output target apparatus.

* * * * *